United States Patent
Takahashi

(10) Patent No.: US 9,913,996 B2
(45) Date of Patent: Mar. 13, 2018

(54) THREE-DIMENSIONAL IMAGE CAPTURE SYSTEM AND PARTICLE BEAM THERAPY SYSTEM

(71) Applicant: Osamu Takahashi, Chiyoda-ku (JP)

(72) Inventor: Osamu Takahashi, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 323 days.

(21) Appl. No.: 14/419,393

(22) PCT Filed: Nov. 5, 2012

(86) PCT No.: PCT/JP2012/078615
§ 371 (c)(1),
(2) Date: Feb. 3, 2015

(87) PCT Pub. No.: WO2014/068785
PCT Pub. Date: May 8, 2014

(65) Prior Publication Data
US 2015/0217137 A1    Aug. 6, 2015

(51) Int. Cl.
*A61N 5/10* (2006.01)
*G01B 11/10* (2006.01)
(Continued)

(52) U.S. Cl.
CPC .......... *A61N 5/1049* (2013.01); *A61N 5/1039* (2013.01); *G01B 11/002* (2013.01);
(Continued)

(58) Field of Classification Search
CPC ....... G01B 11/002; G01B 11/24; G01B 11/10; A61N 5/1039; A61N 5/1043;
(Continued)

(56) References Cited

U.S. PATENT DOCUMENTS 6,279,579 B1 * 8/2001 Riaziat ................ A61N 5/1049
128/897
6,405,072 B1    6/2002 Cosman
(Continued)

FOREIGN PATENT DOCUMENTS

CN          102164636 A    8/2011
JP          55-51219 U     4/1980
(Continued)

OTHER PUBLICATIONS

Japanese Office Action (Notification of Reasons for Refusal) dated Aug. 25, 2015, by the Japanese Patent Office in corresponding Japanese Patent Application No. 2014-544196 with partial English translation thereof. (8 pgs).

(Continued)

*Primary Examiner* — Christine H Matthews
*Assistant Examiner* — Joshua D Lannu
(74) *Attorney, Agent, or Firm* — Buchanan Ingersoll & Rooney PC

(57) ABSTRACT

According to a three-dimensional image capture system of the invention, it includes a three-dimensional measuring device that is placed on a top board and performs image-capturing of a patient to thereby generate three-dimensional-image data, and a three-dimensional-image processing device that generates from the three-dimensional-image data, a three-dimensional image associated with a reference coordinate system with reference to the top board or a floor of a room, and that displays the three-dimensional image. The three-dimensional-image processing device includes a position-information extraction unit that takes a correlation between the reference coordinate system and three-dimensional position information of the patient in the three-dimensional-image data to thereby generate reference-coordinate-system position information of the patient based on (Continued)

the reference coordinate system, and a display unit that displays the three-dimensional image, wherein the display unit displays a reference image and an observed image that are the three-dimensional images captured at different timings.

20 Claims, 15 Drawing Sheets

(51) Int. Cl.
*G01B 11/00* (2006.01)
*G01B 11/24* (2006.01)

(52) U.S. Cl.
CPC .............. *G01B 11/10* (2013.01); *G01B 11/24* (2013.01); *A61N 5/1043* (2013.01); *A61N 2005/1059* (2013.01); *A61N 2005/1074* (2013.01); *A61N 2005/1087* (2013.01); *A61N 2005/1094* (2013.01)

(58) Field of Classification Search
CPC .......... A61N 2005/1094; A61N 5/1049; A61N 2005/1059; A61N 2005/1087; A61N 2005/1074
See application file for complete search history.

(56) References Cited

U.S. PATENT DOCUMENTS

| | | | |
|---|---|---|---|
| 7,502,443 | B1 | 3/2009 | Haynes et al. |
| 2010/0027744 | A1 | 2/2010 | Brown et al. |
| 2011/0101235 | A1 | 5/2011 | Iwata |
| 2011/0121197 | A1 | 5/2011 | Maeda et al. |
| 2013/0056646 | A1 | 3/2013 | Iwata |
| 2013/0253252 | A1 | 9/2013 | Iwata |
| 2014/0077098 | A1* | 3/2014 | Tachikawa ........... A61N 5/1045 250/397 |
| 2014/0235919 | A1 | 8/2014 | Iwata |
| 2015/0087887 | A1 | 3/2015 | Iwata |

FOREIGN PATENT DOCUMENTS

| | | |
|---|---|---|
| JP | 8-206162 A | 8/1996 |
| JP | H08-332235 A | 12/1996 |
| JP | 2002528168 A | 9/2002 |
| JP | 2004-286625 A | 10/2004 |
| JP | 2005-027743 A | 2/2005 |
| JP | 2005-308699 A | 11/2005 |
| JP | 2006-214735 A | 8/2006 |
| JP | 2007-010419 A | 1/2007 |
| JP | 2009-207581 A | 9/2009 |
| JP | 2009-226015 A | 10/2009 |
| JP | 2011-115563 A | 6/2011 |
| JP | 4695231 B2 | 6/2011 |
| TW | 201208728 A1 | 3/2012 |
| WO | 9927839 A2 | 6/1999 |
| WO | WO 00/24333 A1 | 5/2000 |
| WO | 2010012983 A1 | 2/2010 |
| WO | WO 2011/021410 A1 | 2/2011 |

OTHER PUBLICATIONS

Office Action (Rejection Decision) dated Nov. 25, 2015, by the Taiwanese Patent Office in corresponding Taiwanese Patent Application No. 102109986. (7 pgs).
Office Action (Decision of Refusal) dated Jan. 19, 2016, by the Japanese Patent Office in corresponding Japanese Patent Application No. 2014-544196, and a Partial Translation of the Office Action. (6 pages).
Taiwan Office Action dated Jun. 17, 2015 issued in corresponding Taiwan Patent Appln. No. 102109986, with English translation (21 pages).
Chinese Office Action dated Nov. 3, 2016 issued in corresponding Chinese Patent Appln. No. 201280076847.7, with English translation (10 pages).
Office Action dated Jan. 18, 2017, by the Taiwanese Patent Office in corresponding Taiwanese Patent Application No. 102109986, and an English Translation of the Office Action (14 pages).
International Search Report (PCT/ISA/210) dated Dec. 11, 2012, by the Japanese Patent Office as the International Searching Authority for International Application No. PCT/JP2012/078614.
International Search Report (PCT/ISA/210) dated Dec. 11, 2012, by the Japanese Patent Office as the International Searching Authority for International Application No. PCT/JP2012/078615.
Extended European Search Report dated Jun. 9, 2016 issued in corresponding European Patent Appl. No. 12887475.7 (7 pages).
Chinese Office Action dated May 3, 2017, by the Chinese Patent Office in corresponding Chinese Patent Application No. 201280076847.7, and an English Translation of the Office Action. (10 pages).
Office Action dated Oct. 10, 2017 issued by the European Patent Office in corresponding European Patent Application No. 12 887 475.7 (4 pages).

* cited by examiner

THREE-DIMENSIONAL IMAGE CAPTURE SYSTEM AND PARTICLE BEAM THERAPY SYSTEM

TECHNICAL FIELD

The present invention relates to a three-dimensional image capture system for image-capturing a patient laid on a top board of a patient support table, when a radiation, such as an X-ray, a γ-ray, a particle beam or the like, is to be radiated to a diseased site of the patient using a radiation therapy system to thereby perform cancer therapy.

BACKGROUND ART

In recent years, among radiation therapy systems for the purpose of cancer therapy, there have been advanced development and/or construction of a cancer therapy system that utilizes a particle beam of proton, heavy ion, etc. (called, in particular, as a particle beam therapy system) As is well known, according to a particle beam therapy utilizing the particle beam, a cancer diseased site can be irradiated in a concentrated manner as compared to the conventional radiation therapy using an X-ray, a γ-ray, etc., that is, the particle beam can be radiated in a pinpoint manner to be matched to a shape of the diseased site, and thus it is possible to perform the therapy without affecting normal tissues.

In the particle beam therapy, it is important to highly accurately radiate the particle beam to the diseased site such as a cancer. For that purpose, during the particle beam therapy, the patient is fastened using a fastener, etc. in order not to shift his/her position relative to a patient support table in a treatment room (irradiation room). In order to accurately position the diseased site such as a cancer within a radiation exposure region, there is made a setting including roughly emplacing the patient with the aid of a laser pointer, etc., and then, an accurate positioning of the diseased site of the patient is performed using an X-ray image, a CT (Computed Tomography) image or the like.

In Patent Document 1, there is described a treatment table system in which, after being precisely positioned using a three-dimensional diagnosis apparatus (CT apparatus) and while keeping this positioned state, the diseased site is highly accurately positioned at an isocenter of a particle beam therapy system by moving a placing board (top board). Using an isocenter of the three-dimensional diagnosis apparatus (CT apparatus) as a virtual isocenter of the particle beam therapy system, the treatment table system of Patent Document 1 makes positioning so that an image by the three-dimensional diagnosis apparatus is matched to a reference image for positioning. Such a positioning using images, is referred to as an image-matching positioning. After completion of the image-matching positioning at the virtual isocenter, the treatment table system moves the placing board (top board) on which the patient is laid by a movement mechanism of the patient support table, to thereby position the diseased site at the isocenter of the particle beam therapy system.

CITATION LIST

Patent Document

Patent Document 1: Japanese Patent No. 4695231 (FIG. 1)

SUMMARY OF THE INVENTION

Problems to be Solved by the Invention

According to the treatment table system of Patent Document 1, even though the diseased site is precisely positioned through image matching at the isocenter of the three-dimensional diagnosis apparatus (CT apparatus), there is a possibility that the patient is displaced during the movement to the isocenter of the particle beam therapy system. When a displacement in the body position of the patient occurs unintentionally in the process from completion of the image-matching positioning until before the irradiation, and if this is undetected, there is a possibility that a particle beam therapy will be performed with an unintended dose (distribution). In order to solve this problem, it is conceivable to confirm a displacement of the diseased site associated with the displacement in the body position of the patient, by way of X-ray radiography using an X-ray radiographic device including an X-ray source and an X-ray receiver, in such a manner that X-ray images captured at the time of completion of the image-matching positioning and at the time just before the irradiation at an irradiation position, are compared to each other. However, in the case of using X-ray radiography, a problem arises that the patient gets exposed to an X-ray.

This invention is purported to provide a three-dimensional image capture system by which a displacement in the body position of the patient can be confirmed without reception of an unwanted X-ray exposure, in a pre-irradiation period from after the image-matching positioning is performed until before a radiation is radiated to the patient.

Means for Solving the Problems

A three-dimensional image capture system according to the invention comprises: a three-dimensional measuring device that is placed on a top board, and performs image-capturing of a patient without using an X-ray to thereby generate three-dimensional-image data; and a three-dimensional-image processing device that generates from the three-dimensional-image data, a three-dimensional image associated with a reference coordinate system which is a top-board coordinate system with reference to the top board or a room coordinate system with reference to a floor of a room in which a patient support table is placed, and that displays the three-dimensional image. The three-dimensional-image processing device is characterized by including: a position-information extraction unit that takes a correlation between the reference coordinate system and three-dimensional position information of the patient in the three-dimensional-image data, to thereby generate reference-coordinate-system position information of the patient based on the reference coordinate system; and a display unit that displays the three-dimensional image in which the three-dimensional-image data and the reference-coordinate-system position information are consolidated; and wherein the display unit displays a reference image that is the three-dimensional image captured in a condition where a diseased-site region of the patient is being positioned relative to the top board, and an observed image that is the three-dimensional image captured at a timing different to a timing at which the reference image was captured.

Effect of the Invention

In the three-dimensional image capture system according to the invention, the three-dimensional images in which the three-dimensional image data generated by the three-dimensional measuring device not using an X-ray and the reference-coordinate-system position information are consolidated, are captured at different timings, and a reference image and an observed image that are the three-dimensional images captured at the different timings are displayed. Thus, a displacement in the body position of the patient can be confirmed without reception of an X-ray exposure due to X-ray radiography, in a pre-irradiation period from after completion of the image-matching positioning.

MODES FOR CARRYING OUT THE INVENTION

Embodiment 1

Figure 1:
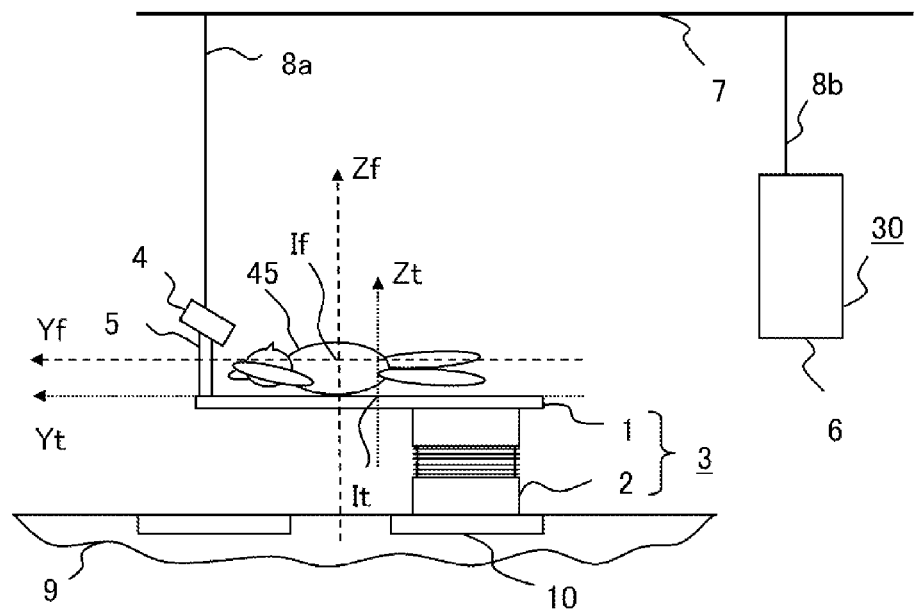
FIG. 1 is a diagram showing an outline configuration of a three-dimensional image capture system according to Embodiment 1 of the invention.
Figure 2:
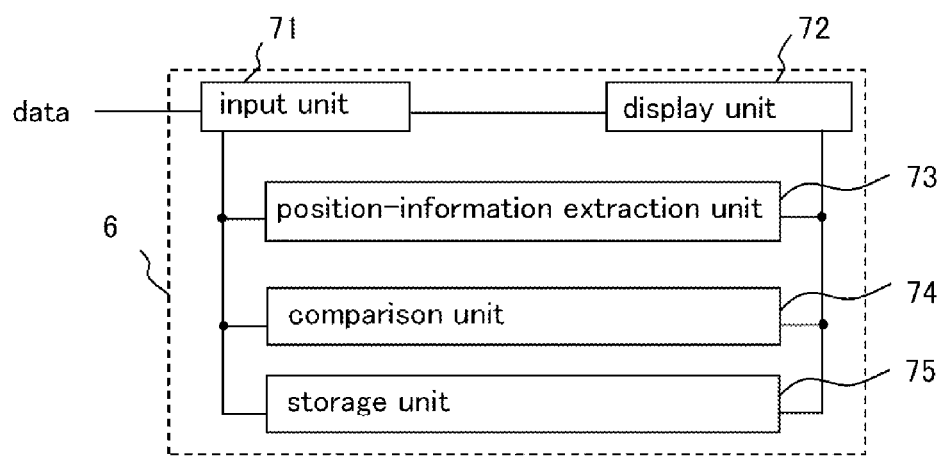
FIG. 2 is a diagram showing a configuration of a three-dimensional-image processing device according to Embodiment 1 of the invention.
Figure 3:
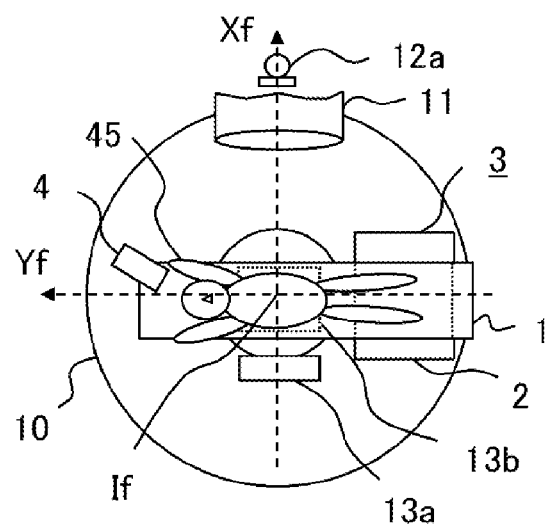
FIG. 3 is a top view illustrating an image-matching positioning according to the invention.
Figure 4:
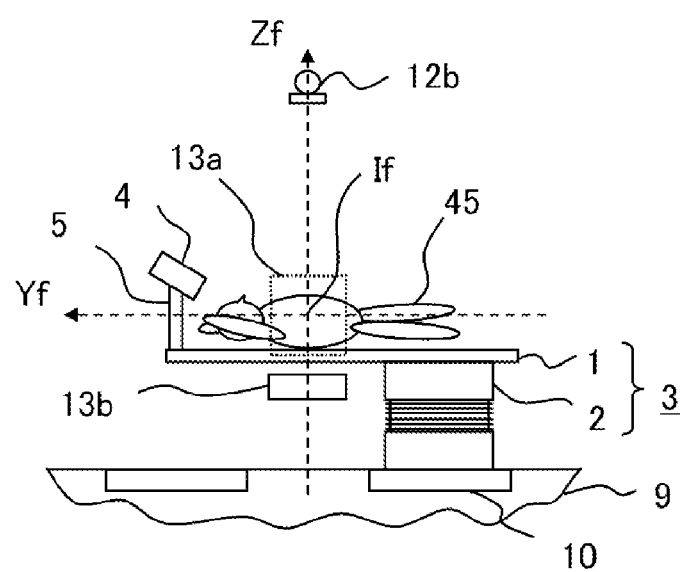
FIG. 4 is a side view illustrating an image-matching positioning according to the invention.
Figure 5:
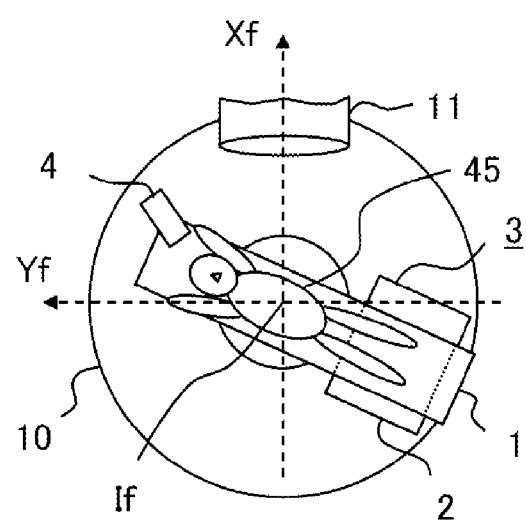
FIG. 5 is a diagram showing a therapeutic irradiation position according to the invention.
Figure 6:
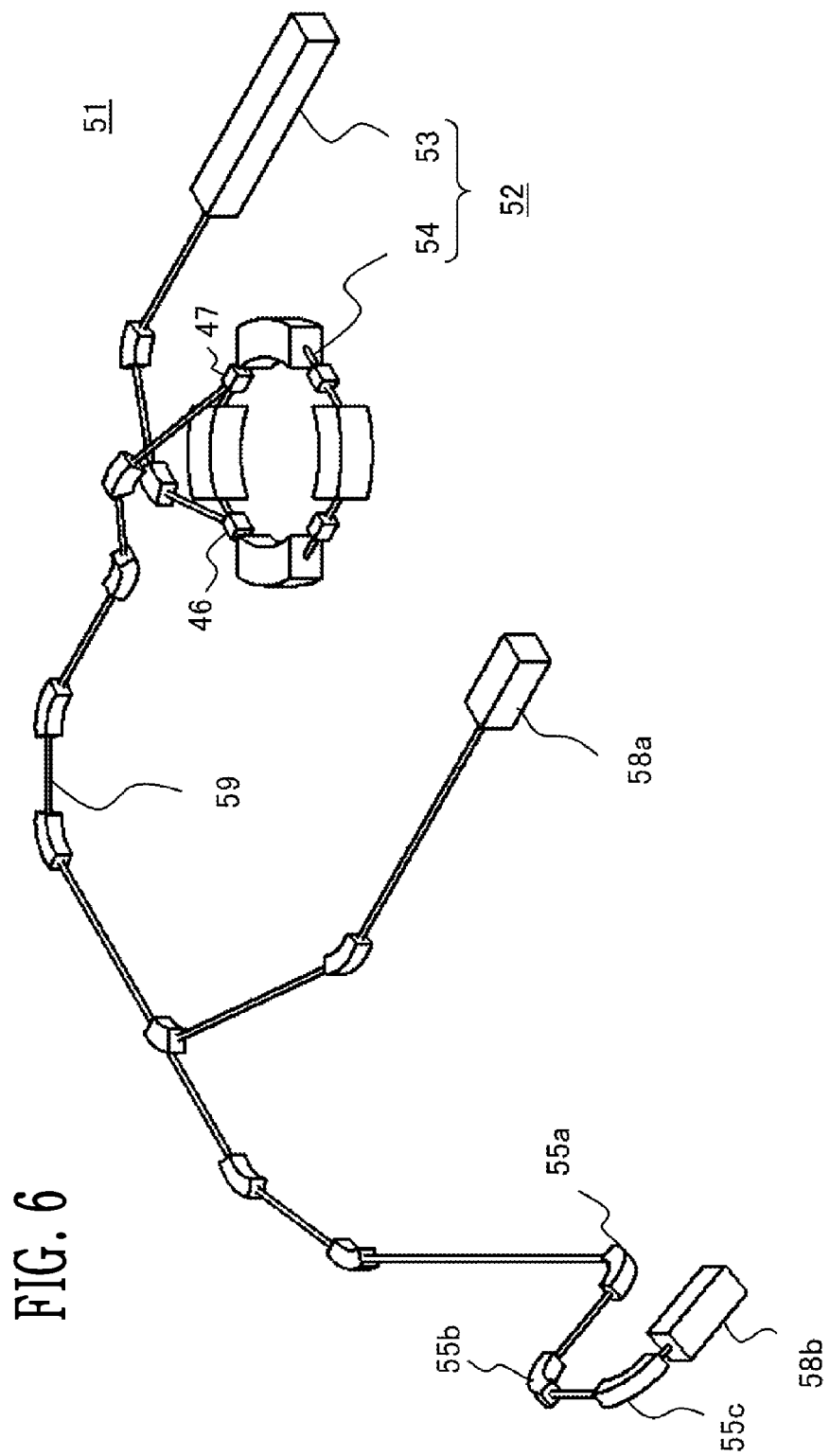
FIG. 6 is a schematic configuration diagram of a particle beam therapy system to which the invention is to be applied.
Figure 7:
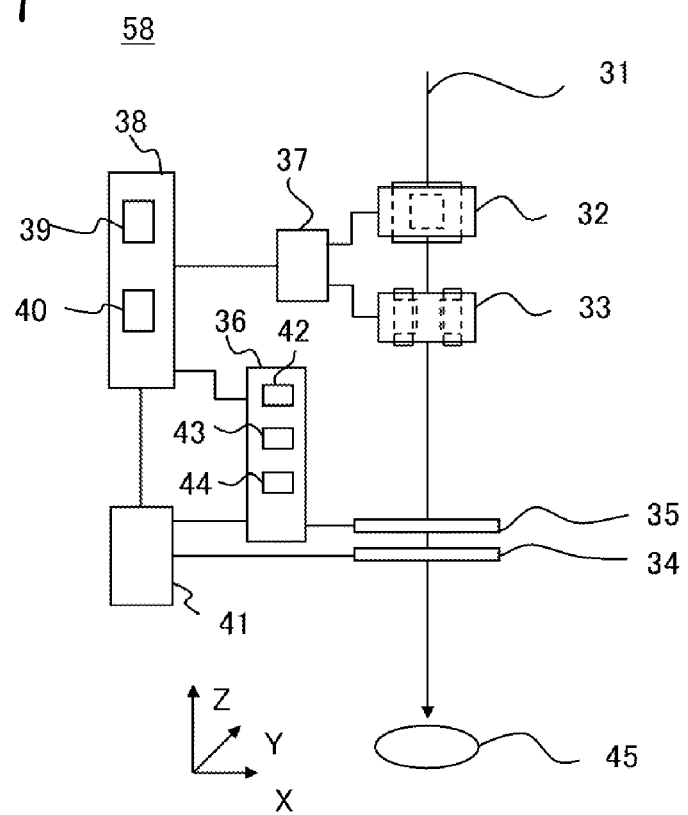
FIG. 7 is a diagram showing a configuration of a particle beam irradiation apparatus in FIG. 6.

FIG. 1 is a diagram showing an outline configuration of a three-dimensional image capture system according to Embodiment 1 of the invention. FIG. 2 is a diagram showing a configuration of a three-dimensional-image processing device according to Embodiment of the invention. FIG. 3 is a top view illustrating an image-matching positioning according to the invention, and FIG. 4 is a side view illustrating an image-matching positioning according to the invention. FIG. 5 is a diagram showing a therapeutic irradiation position according to the invention. FIG. 6 is a schematic configuration diagram of a particle beam therapy system to which the invention is to be applied, and FIG. 7 is a diagram showing a configuration of a particle beam irradiation apparatus in FIG. 6. A three-dimensional image capture system 30 according to Embodiment 1 of the invention includes a patient support table 3 for laying a patient 45, a 3D camera 4 that is a three-dimensional measuring device, and a three-dimensional-image processing device 6. The three-dimensional-image processing device 6 includes an input unit 71, a display unit 72, a position-information extraction unit 73, a comparison unit 74, and a storage unit 75. The patient support table 3 includes a top board 1 on which the patient 45 is laid, and an actuation device 2 for moving the top board 1 to thereby change a position and a posture of the patient 45. The 3D camera 4 is placed on the top board 1 by means of a supporting column 5. The 3D camera 4 is connected to the three-dimensional-image processing device 6 by way of a communication line 8a, a LAN (Local Area Network) communication line 7, and a communication line 8b. The three-dimensional-image data that is captured by the 3D camera 4 is outputted to the three-dimensional-image processing device 6 through the communication line 8a, the LAN communication line 7, and the communication line 8b.

A coordinate system used in the invention will be described. In the invention, a coordinate system with reference to a treatment room and a coordinate system with reference to the top board are used. The coordinate system with reference to the treatment room and the coordinate system with reference to the top board are, respectively, the treatment room-based coordinate system (Fixed reference system) and the top board-based coordinate system (Table top coordinate system) defined in the intentional standards of IEC 61217 by the IEC (International Electrotechnical Commission) or coordinate systems equivalent thereto. The coordinate system with reference to the treatment room is defined, with an isocenter "If" of a radiation irradiation apparatus as an origin, by "Zf" given in a vertical direction that is positive-going upward, "Yf" given in a direction that is positive-going toward the head of the patient 45 in FIG. 1, and "Xf" that provides a right hand system with Zf and Yf. Further, rotations in a clockwise direction with respect to the respective positive-going directions of Xf, Yf and Zf are defined as Φf, ϕf and θf in which the clockwise direction is given as a positive-going direction. The coordinate system with reference to the top board is defined, for example, with a center point "It" in the upper face of the top board 1 as an origin, by "Zt" given in a direction that is positive-going upward along an axis perpendicular to the upper face of the top board 1, "Yt" given as an axis parallel to Yf when the respective rotations by the actuation device 2 for the patient support table 3 are zero, and "Xt" given as an axis parallel to Xf when the respective rotations by the actuation device 2 for the patient support table 3 are zero (see, FIG. 11). Note that, the coordinate system with reference to the treatment room and the coordinate system with reference to the top board are referred to as a treatment-room coordinate system and a top-board coordinate system, respectively, when appropriate. A coordinate system with reference to a floor 9 of the room in which the patient support table 3 is placed, that is like the treatment-room coordinate system, is referred to as a room coordinate system, and the room coordinate system and the top-board coordinate system are referred to collectively as a reference coordinate system.

In Embodiment 1, description will be made using a case where the patient support table 3 is placed on a turn table 10 disposed on the floor 9 of the treatment room, and an irradiation port 11 where a radiation (a charged particle beam 31, etc.) enters into the treatment room from the downstream side of the radiation irradiation apparatus (a particle beam irradiation apparatus 58, etc.) is arranged laterally to the patient 45. At the time of performing a radiation therapy, the patient 45 is fastened using a fastener, etc. (not shown) in order not to shift his/her position relative to the patient support table 3 in the treatment room. There is performed a setting including roughly emplacing the patient with the aid of a laser pointer, etc. Then, using an X-ray radiographic device, an image-matching positioning is performed. For example, as shown in FIG. 3 and FIG. 4, the X-ray radiographic device includes two X-ray sources 12*a*, 12*b* and two X-ray detectors 13*a*, 13*b*. The irradiation port 11 where the radiation enters into the treatment room from the downstream side of the radiation irradiation apparatus is arranged laterally to the patient 45.

The image-matching positioning is performed by controlling the actuation device 2 so that an X-ray image displayed on a monitor screen of the X-ray radiographic device is matched to an X-ray reference image for positioning. Details of a method for image matching will be described later. After completion of the image-matching positioning, the X-ray radiographic device is removed, and the turn table 10 is rotated as shown in FIG. 5 to thereby move the patient 45 to a therapeutic irradiation position. Thereafter, a therapy is performed by radiating the radiation to a diseased site of the patient 45.

As an example of the radiation therapy system, a particle beam therapy system 51 and the particle beam irradiation apparatus 58 will be described using FIG. 6 and FIG. 7. The particle beam therapy system 51 includes a beam generation apparatus 52, a beam transport system 59, and the particle beam irradiation apparatuses 58*a*, 58*b*. The beam generation apparatus 52 includes an ion source (not shown), a pre-accelerator 53, and a charged particle accelerator 54. The particle beam irradiation apparatus 58*b* is placed in a rotating gantry (not shown). The particle beam irradiation apparatus 58*a* is placed in a treatment room having no rotating gantry. The role of the beam transport system 59 is to communicate between the charged particle accelerator 54 and the particle beam irradiation apparatuses 58*a*, 58*b*. The beam transport system 59 is partly placed in the rotating gantry (not shown) and includes, at that part, a plurality of deflection electromagnets 55*a*, 55*b*, 55*c*.

The charged particle beam that is a particle beam, such as a proton beam, etc., generated by the ion source, is accelerated by the pre-accelerator 53 and entered into the charged particle accelerator 54 through an injection device 46. The charged particle accelerator 54 is a synchrotron, for example. The charged particle beam is accelerated up to a given energy. The charged particle beam emitted from an emission device 47 of the charged particle accelerator 54, is transported through the beam transport system 59 to the particle beam irradiation apparatuses 58*a*, 58*b*. The particle beam irradiation apparatuses 58*a*, 58*b* each radiate the charged particle beam to the diseased site of the patient 45. For the particle beam irradiation apparatuses, numeral 58 is used collectively, and numerals 58*a*, 58*b* are used when they are to be described distinctively.

The charged particle beam 31 generated by the beam generation apparatus 52 and accelerated up to the given energy, is brought through the beam transport system 59 to the particle beam irradiation apparatus 58. In FIG. 7, the particle beam irradiation apparatus 58 includes: X-direction scanning electromagnet 32 and Y-direction scanning electromagnet 33 which scan the charged particle beam 31, respectively in an X-direction and a Y-direction that are directions perpendicular to the charged particle beam 31; a position monitor 34; a dose monitor 35; a dose-data converter 36; a beam-data processing device 41; a scanning-electromagnet power source 37; and an irradiation management device 38 for controlling the particle beam irradiation apparatus 58. The irradiation management device 38 includes an irradiation control calculator 39 and an irradiation control device 40. The dose-data converter 36 includes a trigger generation unit 42, a spot counter 43 and an inter-spot counter 44. Note that in FIG. 7, the travelling direction of the charged particle beam 31 is a direction of −Z.

The X-direction scanning electromagnet 32 is a scanning electromagnet for scanning the charged particle beam 31 in the X-direction, and the Y-direction scanning electromagnet 33 is a scanning electromagnet for scanning the charged particle beam 31 in the Y-direction. With respect to the charged particle beam 31 scanned by the X-direction scanning electromagnet 32 and the Y-direction scanning electromagnet 33, the position monitor 34 detects beam information for calculating a passing position (gravity center position) and a size of the beam that passes therethrough. The beam-data processing device 41 calculates the passing position (gravity center position) and the size of the charged particle beam 31 on the basis of the beam information that comprises a plurality of analog signals detected by the position monitor 34. Further, the beam-data processing device 41 generates an abnormality detection signal indicative of a position abnormality and/or a size abnormality of the charged particle beam 31, and outputs the abnormality detection signal to the irradiation management device 38.

The dose monitor 35 detects the dose of the charged particle beam 31. The irradiation management device 38 controls the irradiation position of the charged particle beam 31 in the diseased site of the patient 45 on the basis of treatment plan data prepared by an unshown treatment plan device, and moves the charged particle beam 31 to a next irradiation position when the dose having been measured by the dose monitor 35 and converted by the dose-data converter 36 into digital data, reaches a desired dose. The scanning-electromagnet power source 37 changes setup currents for the X-direction scanning electromagnet 32 and the Y-direction scanning electromagnet 33 on the basis of control inputs (commands) outputted from the irradiation management device 38 for the X-direction scanning electromagnet 32 and the Y-direction scanning electromagnet 33.

Here, the scanning irradiation method of the particle beam irradiation apparatus 58 is assumed to be a raster-scanning irradiation method in which the charged particle beam 31 is not stopped when the irradiation position of the charged particle beam 31 is changed, that is a method in which the beam irradiation position moves between spot positions successively like a spot-scanning irradiation method. The spot counter 43 serves to measure an amount of irradiation dose during when the beam irradiation position of the charged particle beam 31 is staying. The inter-spot counter 44 serves to measure an amount of irradiation dose during when the beam irradiation position of the charged particle beam 31 is moving. The trigger generation unit 42 serves to generate a dose completion signal when the dose of the charged particle beam 31 at a beam irradiation position reaches the desired irradiation dose.

Figure 8:
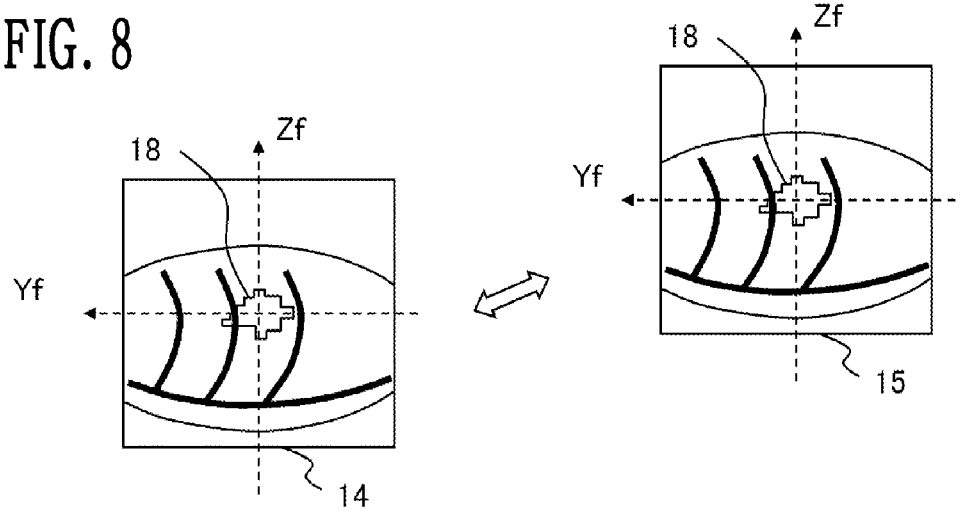
FIG. 8 is a diagram illustrating an image matching in YZ plane according to the invention.
Figure 9:
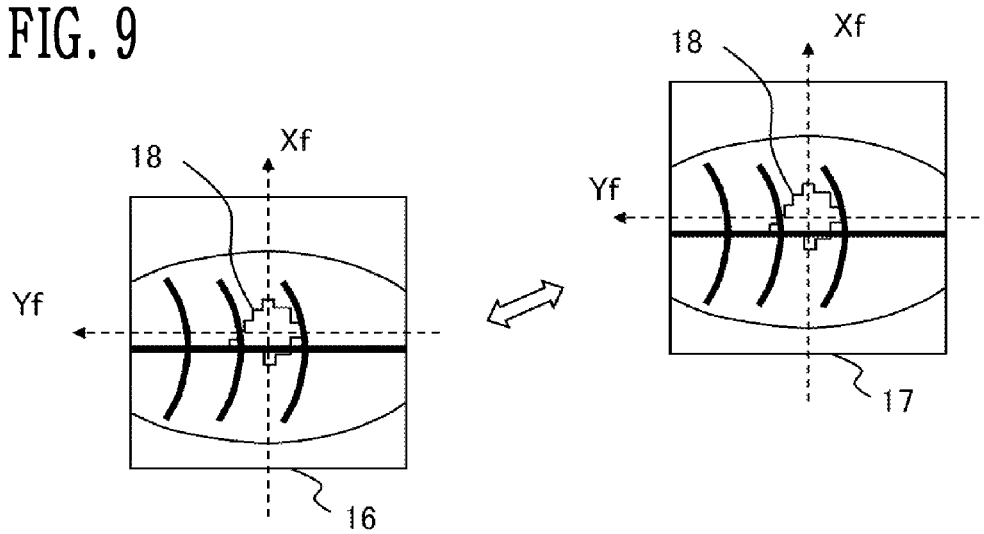
FIG. 9 is a diagram illustrating an image matching in XY plane according to the invention.

Using FIG. 8 and FIG. 9, the method for image matching will be described. FIG. 8 is a diagram illustrating an image matching in YZ plane that is a flat plane perpendicular to an Xf-axis in the Xf direction, and FIG. 9 is a diagram illustrating an image matching in XY plane that is a flat plane perpendicular to a Zf-axis in the Zf direction. An X-ray image 14 in FIG. 8 is an X-ray image captured by the X-ray source 12a and the X-ray detector 13a. An X-ray image 16 in FIG. 9 is an X-ray image captured by the X-ray source 12b and the X-ray detector 13b. An X-ray reference image 15 is an X-ray reference image in YZ plane that has been prepared, for example, from CT cross-sectional images captured when a treatment plan was prepared. An X-ray reference image 17 is an X-ray reference image in XY plane that has been prepared, for example, from CT cross-sectional images captured when the treatment plan was prepared.

An operator such as a technologist, a doctor or the like, controls the actuation device 2 so that a diseased-site region 18 in the X-ray images 14, 16 displayed on the monitor screen of the X-ray radiographic device, is matched to a diseased-site region 18 in the X-ray reference images 15, 17, to thereby perform the image-matching positioning. In the case of Embodiment 1, at the time of performing the image-matching positioning, the patient 45 is in a posture similar to that in a coplanar irradiation in which a radiation is radiated from a direction parallel to a flat plane that is perpendicular to a body axis of the patient 45 (an axis in the Yf direction in FIG. 1). That is, if a radiation is radiated from the irradiation port 11 shown in FIG. 3 to the patient 45, this results in performing a coplanar irradiation of the patient 45. A position of the patient that provides the posture similar to that in a coplanar irradiation is referred to as a coplanar position. The CT cross-sectional images are a set of cross-sectional images captured for cross sections of the patient 45 perpendicular to the body axis. That is, the CT cross-sectional images are those captured when the patient 45 is at the coplanar position.

Since the X-ray images 14, 16 are those captured when the patient 45 is at the coplanar position, the image-matching positioning in Embodiment 1 is executed, for example, when the patient 45 is in the coplanar position. Then, as shown in FIG. 5, the turn table 10 is rotated to thereby move the patient 45 to the therapeutic irradiation position, so that a therapy is performed by radiating the radiation to the diseased site of the patient 45. Such an irradiation is not a coplanar irradiation but is a non-coplanar irradiation in which a radiation is radiated from a direction crossing a flat plane that is perpendicular to the body axis of the patient 45.

Next, an operation of the three-dimensional image capture system 30 of Embodiment 1 will be described. The 3D camera is, for example, an optical stereo camera, and can measure three-dimensional positions (coordinates) for respective portions of an imaging object, and thus can capture a three-dimensional image having a deep appearance. The three-dimensional-image processing device 6 acquires at the input unit 71 the three-dimensional-image data (data shown in FIG. 2) outputted from the 3D camera 4, and outputs the three-dimensional capture image to the display unit 72. The three-dimensional-image processing device 6 takes a correlation, at the position-information extraction unit 73, between the top-board coordinate system (reference coordinate system) with reference to the top board 1 and three-dimensional position information of the patient 45, to thereby generate position information based on the top-board coordinate system of the patient given as the imaging object. That is, it calculates the coordinates of the patient 45. For example, it generates position information of the patient 45 using as a starting point a coordinate of a corner of the top board 1 in the three-dimensional capture image. The position information based on the top-board coordinate system of the patient 45 is top-board-coordinate-system position information (reference-coordinate-system position information).

The three-dimensional capture image displayed on the display unit 72 is caused to be associated with the above position information of the patient 45. Thus, the three-dimensional capture image displayed on the display unit 72 is associated with the top-board coordinate system, and is given as a three-dimensional capture image in which the three-dimensional-image data and the top-board-coordinate-system position information are consolidated. Further, the three-dimensional-image processing device 6 stores in the storage unit 75, a plurality of three-dimensional-image data inputted from the input unit 71. The three-dimensional-image processing device 6 compares with each other, at the comparison unit 74, two specified three-dimensional-image data, that is, two three-dimensional-image data having been captured at different timings, and displays the comparison result on the display unit 72.

Figure 10:
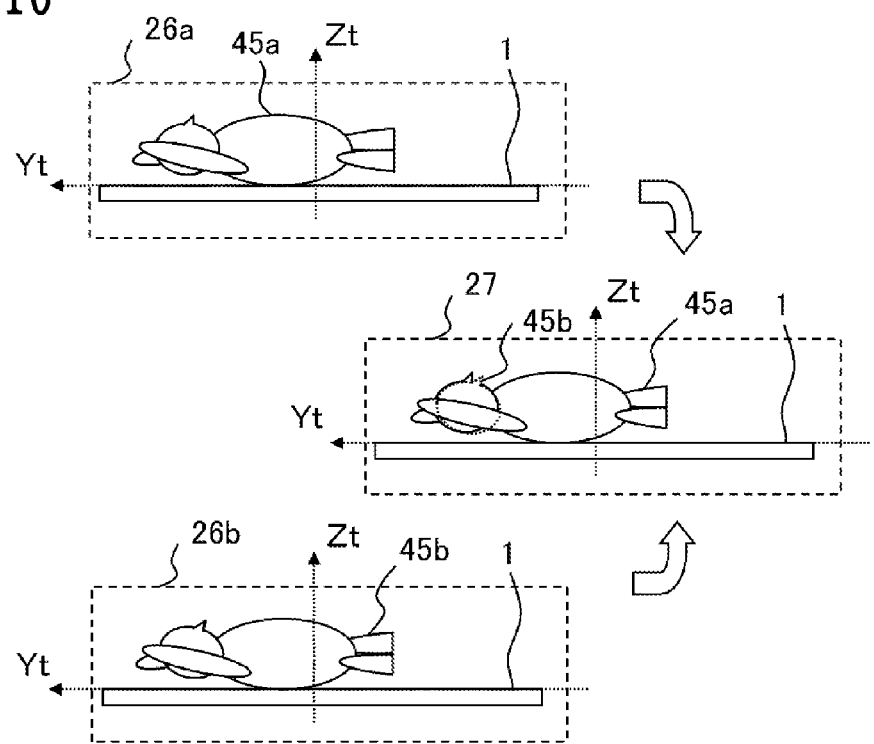
FIG. 10 is a diagram showing a three-dimensional capture image according to Embodiment 1 of the invention.
Figure 11:
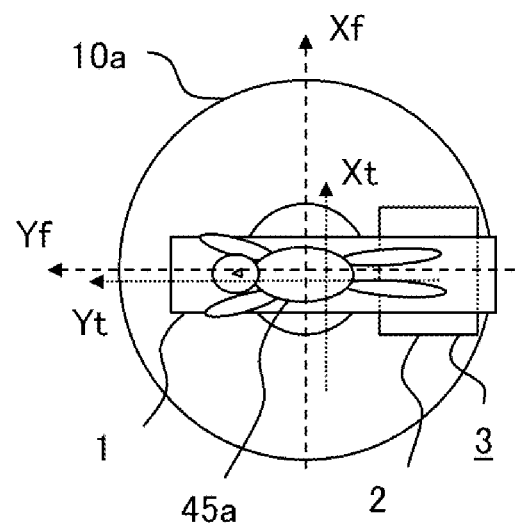
FIG. 11 is a diagram showing a patient at the time of reference image-capturing in FIG. 10.
Figure 12:
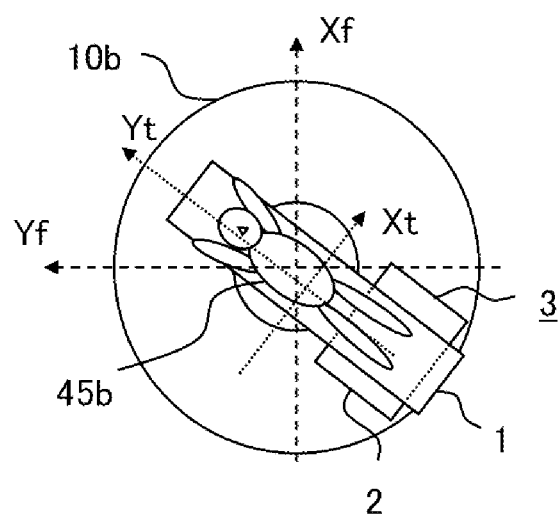
FIG. 12 is a diagram showing a patient at the time of posture observation in FIG. 10.

FIG. 10 is a diagram showing a three-dimensional capture image according to Embodiment 1 of the invention. FIG. 11 is a diagram showing a patient at the time of reference image-capturing in FIG. 10, and FIG. 12 is a diagram showing the patient at the time of posture observation in FIG. 10. After completion of the image-matching positioning, the three-dimensional image of the patient 45 is captured by the 3D camera 4 so that the periphery around the diseased site is at least included therein. A patient 45a shown in FIG. 11 is the patient at the time of reference image-capturing after completion of the image-matching positioning. A three-dimensional capture image 26a captured at that time is displayed on the display unit 72. FIG. 10 shows a case where the whole of the patient 45 can not be image-captured by a single 3D camera 4, so that the patient 45 is partly displayed. Note that, in FIG. 10, a top-board outline is displayed as being overlapped with the top board 1 and the three-dimensional capture image of the patient 45 is displayed in such a size that the whole length of the top board 1 can be seen. Note that, for the three-dimensional capture images, numeral 26 is used collectively, and numerals 26*a*, 26*b*, 26*c*, 26*d*, 26*e*, 26*f* are used when they are to be described distinctively.

Then, the turn table 10 is rotated to thereby move the patient 45 to the therapeutic irradiation position, and thereafter, the three-dimensional image of the patient 45 is captured by the 3D camera 4 so that the periphery around the diseased site is at least included therein. Since the 3D camera 4 is fixed to the top board, the patient 45 is image-captured in the same imaging region as that at the time of reference image-capturing, unless the height or the direction of the 3D camera 4 is changed. A patient 45*b* shown in FIG. 12 is the patient at the therapeutic irradiation position at the time of observed-image capturing. A three-dimensional capture image 26*b* captured at that time is displayed on the display unit 72.

The comparison unit 74 compares the three-dimensional-image data corresponding to the reference image and the three-dimensional-image data corresponding to the observed image with each other according to the top-board coordinate system, and displays the comparison result on the display unit 72, for example, as a three-dimensional comparative capture image 27 in FIG. 10. The three-dimensional comparative capture image 27 is resulted from displaying a portion of the three-dimensional capture image 26*b* as the observed image (a head region of the patient 45*b* indicated by a broken line), that is mismatched from the three-dimensional capture image 26*a* as the reference image, to be overlapped with the three-dimensional capture image 26*a*. The portion of the three-dimensional capture image 26*b* as the observed image, that is mismatched from the three-dimensional capture image 26*a* as the reference image, is an example of a differential image that is a difference according to the top-board coordinate system (reference coordinate system) between the three-dimensional-image data corresponding to the reference image and the three-dimensional-image data corresponding to the observed image.

Figure 13:
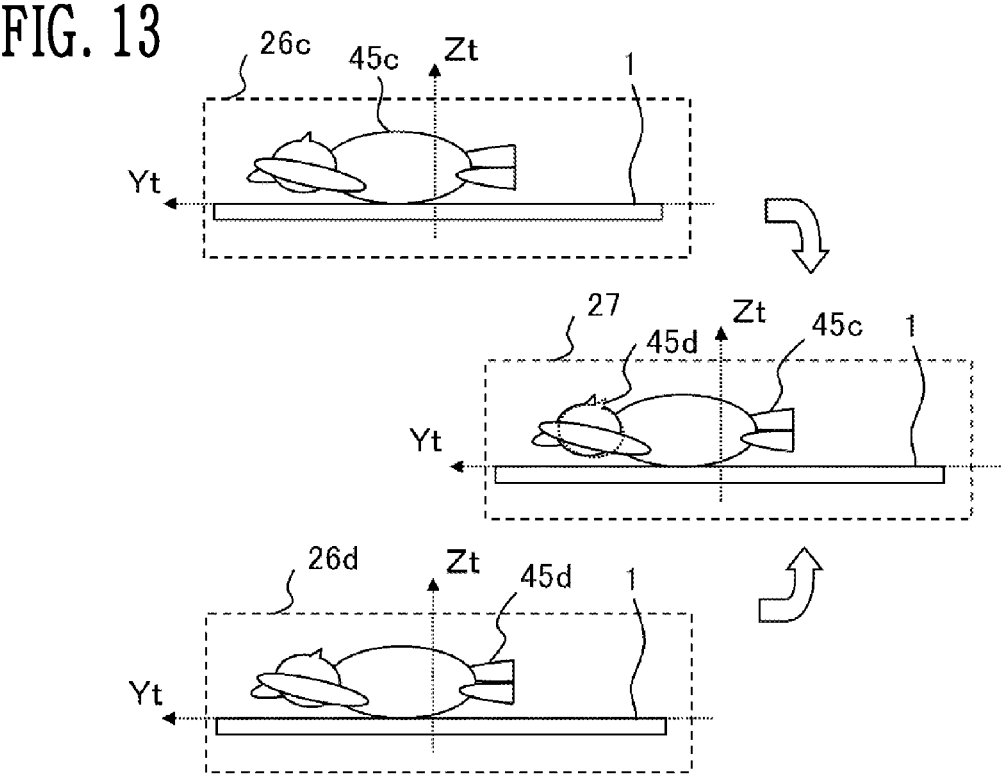
FIG. 13 is a diagram showing another three-dimensional capture image according to Embodiment 1 of the invention.
Figure 14:
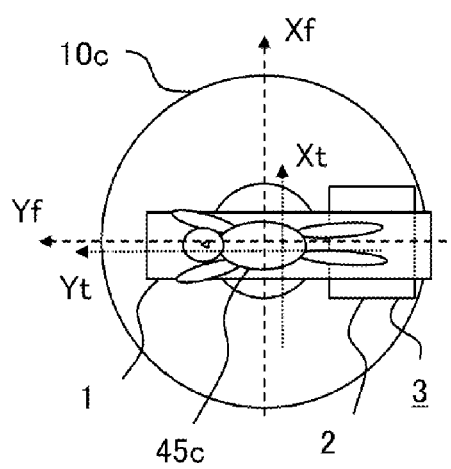
FIG. 14 is a diagram showing a patient at the time of reference image-capturing in FIG. 13.
Figure 15:
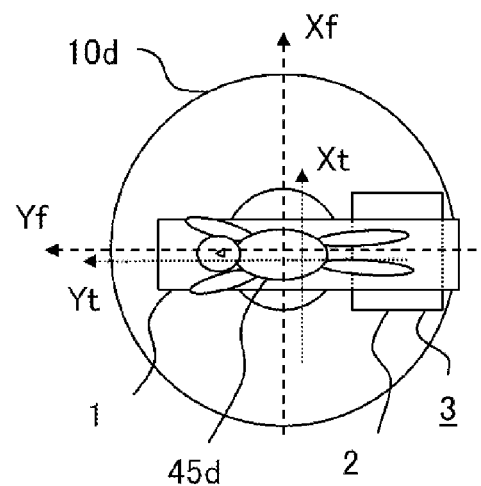
FIG. 15 is a diagram showing a patient at the time of posture observation in FIG. 13.

Meanwhile, the observed image may be captured when the top board 1 has been not yet moved, at a different timing to that of the reference image. FIG. 13 is a diagram showing another three-dimensional capture image according to Embodiment 1 of the invention. FIG. 14 is a diagram showing a patient at the time of reference image-capturing in FIG. 13, and FIG. 15 is a diagram showing the patient at the time of posture observation in FIG. 13. After completion of the image-matching positioning, the three-dimensional image of the patient 45 is captured by the 3D camera 4 as similar to the above. A patient 45*c* shown in FIG. 14 is the patient at the time of reference image-capturing after completion of the image-matching positioning. The three-dimensional capture image 26*c* captured at that time is displayed on the display unit 72. Then, a three-dimensional image of the patient 45 is captured at a different timing to that of the reference image. A patient 45*d* shown in FIG. 15 is the patient at the time of observed-image capturing that is made at a different timing to that of the reference image. The three-dimensional capture image 26*d* captured at that time is displayed on the display unit 72. Similarly to FIG. 10, FIG. 13 shows a case where the whole of the patient 45 can not be image-captured by a single 3D camera 4, so that the patient 45 is partly displayed. Also in FIG. 13, a top-board outline is displayed as being overlapped with the top board 1 and the three-dimensional capture image of the patient 45 is displayed in such a size that the whole length of the top board 1 can be seen.

The comparison unit 74 compares the three-dimensional-image data corresponding to the reference image and the three-dimensional image data corresponding to the observed image with each other according to the top-board coordinate system, and displays the comparison result on the display unit 72, for example, as the three-dimensional comparative capture image 27 in FIG. 13. The three-dimensional comparative capture image 27 is resulted from displaying a portion of the three-dimensional capture image 26*d* as the observed image (a head region of the patient 45*d* indicated by a broken line), that is mismatched from the three-dimensional capture image 26*c* as the reference image, to be overlapped with the three-dimensional capture image 26*c*.

The different timing to that of the reference image is, for example, a timing with a lapse of time in a period before the patient 45 is moved to the therapeutic irradiation position. When an unacceptable displacement in the body position of the patient 45 is confirmed at that time, the image-matching positioning can be re-performed before the turn table 10 is rotated. According to the image-matching positioning re-performed before the turn table 10 is rotated, it is possible to reduce the time before the radiation is radiated to the patient 45, as compared to the case where an unacceptable displacement in the body position of the patient 45 is confirmed at the therapeutic irradiation position and then the image-matching positioning is re-performed after the patient is returned back to the coplanar position. Note that the different timing to that of the reference image may be just before the therapeutic irradiation, when a coplanar irradiation is performed.

The three-dimensional image capture system 30 of Embodiment 1 can confirm a displacement in the body position of the patient 45 after completion of the image-matching positioning, without using an X-ray radiographic device. By applying the three-dimensional image capture system 30 of Embodiment 1 to a radiation therapy system, it is possible to prevent the patient 45 from receiving an unwanted X-ray exposure in a pre-irradiation period from after the image-matching positioning is performed until before the radiation is radiated to the patient 45. The radiation therapy system (particle beam therapy system 51, etc.) provided with the three-dimensional image capture system 30 of Embodiment 1 can confirm a displacement in the body position of the patient 45 without reception of an X-ray exposure, in a pre-irradiation period from after the image-matching positioning is performed until before the radiation is radiated to the patient 45. Thus, the radiation therapy is prevented from being performed with an unintended dose (distribution), thereby making it possible to radiate the radiation with a dose distribution planned in the treatment plan. Further, a displacement in the body position of the patient 45 can be confirmed even in the case of a Zf-axis rotation (isocentric rotation) of the patient support table 3, for example, in a non-coplanar irradiation, or in the case of associating a large movement of the top board 1, such as, the CT-based positioning as described in BACKGROUND ART or the prior-room positioning. The prior-room positioning is that in which the patient 45 is beforehand subjected to an image-matching positioning in a room different to the treatment room in which he/she is to be treated, then the top board 1 and the patient 45 are moved, while keeping the top board 1 and the posture of the patient 45, so that the top board 1 on which the patient 45 is laid is placed on the actuation device 2 of the patient support table 3 in the treatment room, and then the actuation device 2 is controlled based on information of a position/posture at the time of the image-matching positioning, to thereby reproduce the position/posture at the time of the image-matching positioning.

In the above description, a case is described where the comparison unit 74 compares with each other, the first three-dimensional-image data that is three-dimensional-image data captured at a first timing and the second three-dimensional-image data that is three-dimensional-image data captured at a timing later than the first timing, according to the top-board coordinate system (reference coordinate system), and displays the comparison result on the display unit 72. As is not limited thereto, another method may be used that confirms a displacement in the body position of the patient 45 in the pre-irradiation period from after completion of the image-matching positioning. The three-dimensional image capture system 30 may be configured to display on the display unit 72, the two three-dimensional capture images (three-dimensional images) 26a, 26b captured at different timings to be overlapped with each other in such a manner that their same coordinate in the top-board coordinate system (reference coordinate system) is placed at the same position. Even in this case, a displacement in the body position of the patient 45 can be confirmed.

As described above, according to the three-dimensional image capture system 30 of Embodiment 1, it includes: the three-dimensional measuring device (3D camera 4) that is placed on the top board 1 and performs image-capturing of the patient 45 without using an X-ray to thereby generate the three-dimensional-image data; and the three-dimensional-image processing device 6 that generates from the three-dimensional-image data, the three-dimensional image (three-dimensional capture image 26) associated with the reference coordinate system that is the top-board coordinate system with reference to the top board 1, and that displays the three-dimensional image (three-dimensional capture image 26). According to the three-dimensional image capture system 30 of Embodiment 1, the three-dimensional-image processing device 6 is characterized by including: the position-information extraction unit 73 that takes a correlation between the reference coordinate system and the three-dimensional position information of the patient 45 in the three-dimensional-image data, to thereby generate the reference-coordinate-system position information of the patient 45 based on the reference coordinate system; and the display unit 72 that displays the three-dimensional image (three-dimensional capture image 26) in which the three-dimensional-image data and the reference-coordinate-system position information are consolidated; wherein the display unit 72 displays the two three-dimensional images (three-dimensional capture images 26) captured at different timings. Thus, it is possible to confirm a displacement in the body position of the patient 45 in a pre-irradiation period from after completion of the image-matching positioning, without the patient 45 receiving an X-ray exposure by X-ray radiography.

According to the particle beam therapy system 51 of Embodiment 1, it includes: the beam generation apparatus 52 that generates the charged particle beam 31 and accelerates it up to a given energy using the accelerator (charged particle accelerator 54); the beam transport system 59 that transports the charged particle beam 31 accelerated by the beam generation apparatus 52; the particle beam irradiation apparatus 58 that radiates the charged particle beam 31 transported by the beam transport system 59 to the patient 45; and the three-dimensional image capture system 30 that image-captures the patient 45 to which the charged particle beam 31 is to be radiated. The three-dimensional image capture system 30 included in the particle beam therapy system 51 of Embodiment 1 includes: the three-dimensional measuring device (3D camera 4) that is placed on the top board 1 and performs image-capturing of the patient 45 without using an X-ray to thereby generate the three-dimensional-image data; and the three-dimensional-image processing device 6 that generates from the three-dimensional-image data, the three-dimensional image (three-dimensional capture image 26) associated with the reference coordinate system that is the top-board coordinate system with reference to the top board 1, and that displays the three-dimensional image (three-dimensional capture image 26). According to the particle beam therapy system 51 of Embodiment 1, the three-dimensional-image processing device is characterized by including: the position-information extraction unit 73 that takes a correlation between the reference coordinate system and the three-dimensional position information of the patient 45 in the three-dimensional-image data, to thereby generate the reference-coordinate-system position information of the patient 45 based on the reference coordinate system; and the display unit 72 that displays the three-dimensional image (three-dimensional capture image 26) in which the three-dimensional-image data and the reference-coordinate-system position information are consolidated; wherein the display unit 72 displays the two three-dimensional images (three-dimensional capture images 26) captured at different timings. Thus, it is possible to confirm a displacement in the body position of the patient 45 in a period from after completion of the image-matching positioning until just before the irradiation, without the patient 45 receiving an X-ray exposure by X-ray radiography, so that the radiation can be radiated with a dose distribution planned in the treatment plan.

Embodiment 2

Figure 16:
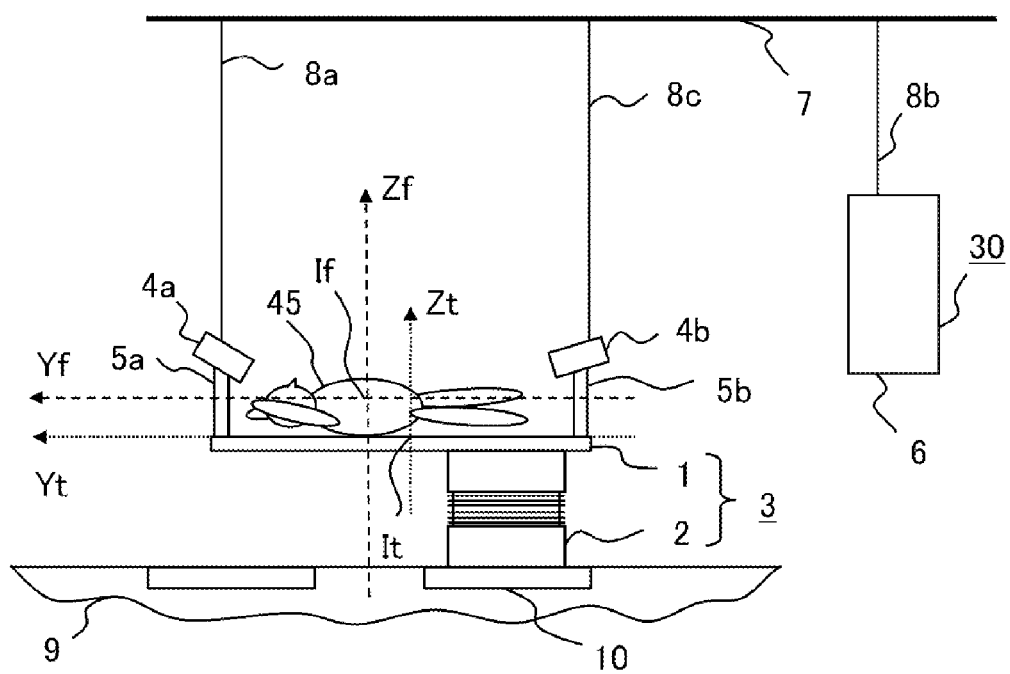
FIG. 16 is a diagram showing an outline configuration of a three-dimensional image capture system according to Embodiment 2 of the invention.
Figure 17:
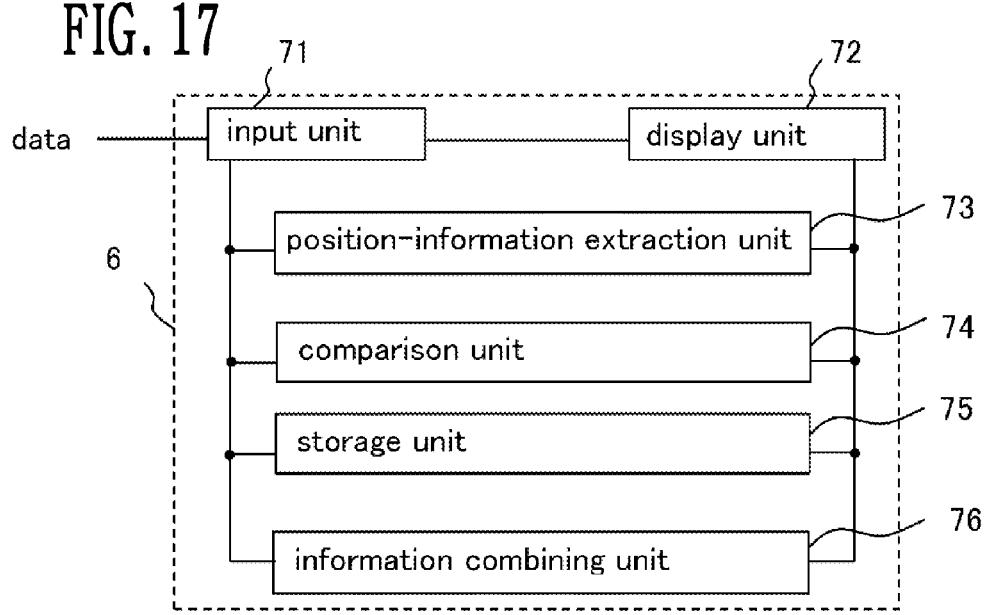
FIG. 17 is a diagram showing a configuration of a three-dimensional-image processing device according to Embodiment 2 of the invention.
Figure 18:
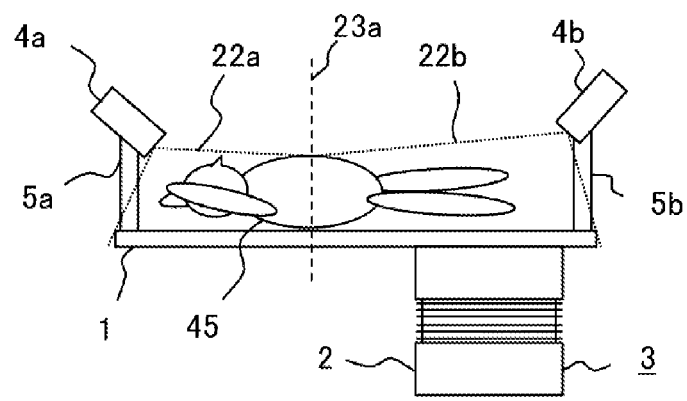
FIG. 18 is a diagram showing imaging regions according to Embodiment 2 of the invention.
Figure 19:
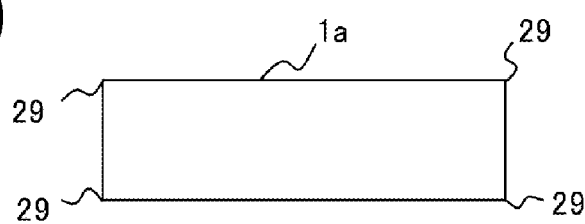
FIG. 19 is a diagram showing positional references of a top board according to Embodiment 2 of the invention.

In Embodiment 2, it is so configured that, when a plurality of imaging regions are captured by a single 3D camera 4 or when a plurality of imaging regions are captured by a plurality of 3D cameras 4, a displacement in the body position of the patient 45 can be confirmed by combining the captured information from the plurality of imaging regions. FIG. 16 is a diagram showing an outline configuration of a three-dimensional image capture system according to Embodiment 2 of the invention, and FIG. 17 is a diagram showing a configuration of a three-dimensional-image processing device according to Embodiment 2 of the invention. FIG. 18 is a diagram showing the imaging regions according to Embodiment 2 of the invention, and FIG. 19 is a diagram showing positional references of a top board according to Embodiment 2 of the invention.

The three-dimensional image capture system 30 of Embodiment 2 shown in FIG. 16 includes two 3D cameras 4a, 4b. The 3D camera 4a is placed on the top board 1 by means of a supporting column 5a, and the 3D camera 4b is placed on the top board 1 by means of a supporting column 5b. The 3D camera 4a is connected to the LAN communication line 7 through the communication line 8a, and the 3D camera 4b is connected to the LAN communication line 7 through a communication line 8c. The three-dimensional-image processing device 6 of Embodiment 2 is different in that an information combining unit 76 is added thereto, relative to the three-dimensional-image processing device 6 of Embodiment 1. For the 3D cameras, numeral 4 is used collectively, and numerals 4a, 4b are used when they are to be described distinctively. For the supporting columns, numeral 5 is used collectively, and numerals 5*a*, 5*b* are used when they are to be described distinctively.

As shown in FIG. 18, the patient 45 is image-captured in two imaging regions of an imaging region 22*a* given from a broken line 23*a* toward the head side and an imaging region 22*b* given from the broken line 23*a* toward the leg side. The 3D camera 4*a* captures the imaging object in the imaging region 22*a*, and the 3D camera 4*b* captures the imaging object in the imaging region 22*b*. Note that there is an overlapped portion between regions to be actually captured by the 3D cameras 4*a*, 4*b*, and at the overlapped portion, there is a data boundary in a combined three-dimensional capture image to be described later. The broken line 23*a* shown in FIG. 18 corresponds to the data boundary. Using the corners of the top board 1 as positional references 29 shown in FIG. 19, position information based on the top-board coordinate system of the patient 45 is generated in the position-information extraction unit 73. The data boundary can be specified by utilizing the position information based on the top-board coordinate system of the patient 45. Note that in FIG. 19, the numeral 1*a* is given for the top board, the reason of which is to differentiate it from another top board to be described later. For the top boards, numeral 1 is used collectively.

An operation of the three-dimensional-image processing device 6 of Embodiment 2 will be described. The three-dimensional-image processing device 6 acquires at the input unit 71, the three-dimensional-image data (data shown in FIG. 17) outputted from the 3D cameras 4*a*, 4*b*. The two three-dimensional-image data outputted from the 3D cameras 4*a*, 4*b* are those having been captured at the same timing or substantially the same timing. The two three-dimensional-image data captured within a time period during which the mechanical errors and the manners of the patient are regarded as substantially the same, are those having been captured at substantially the same timing. The three-dimensional-image processing device 6 takes, at the position-information extraction unit 73, a correlation between the top-board coordinate system with reference to the top board 1 and the three-dimensional position information of the patient 45, for each of the three-dimensional-image data of the respective 3D cameras 4*a*, 4*b*, to thereby generate the position information based on the top-board coordinate system of the patient 45 given as the imaging object. The position-information extraction unit 73 generates the position information of the patient 45 using as starting points, the coordinates of the positional references 29 shown in FIG. 19. The three-dimensional-image processing device 6 generates at the information combining unit 76, combined three-dimensional-image data in which the three-dimensional-image data of the 3D camera 4*a* and the three-dimensional-image data of the 3D camera 4*b* are combined, to thereby output a three-dimensional capture image thus combined (combined three-dimensional image) to the display unit 72.

The three-dimensional capture image (combined three-dimensional image) displayed on the display unit 72 is based on the combined three-dimensional-image data that is associated with the top-board coordinate system. Thus, the three-dimensional capture image displayed on the display unit 72 is associated with the top-board coordinate system, and is given as a three-dimensional capture image in which the combined three-dimensional-image data and the top-board-coordinate-system position information are consolidated. Further, the three-dimensional-image processing device 6 stores in the storage unit 75, a plurality of three-dimensional-image data inputted from the input unit 71 and the combined three-dimensional-image data. The three-dimensional-image processing device 6 compares with each other, at the comparison unit 74, two specified three-dimensional-image data, that is, two three-dimensional-image data having been captured at different timings, and displays the comparison result on the display unit 72.

Figure 20:
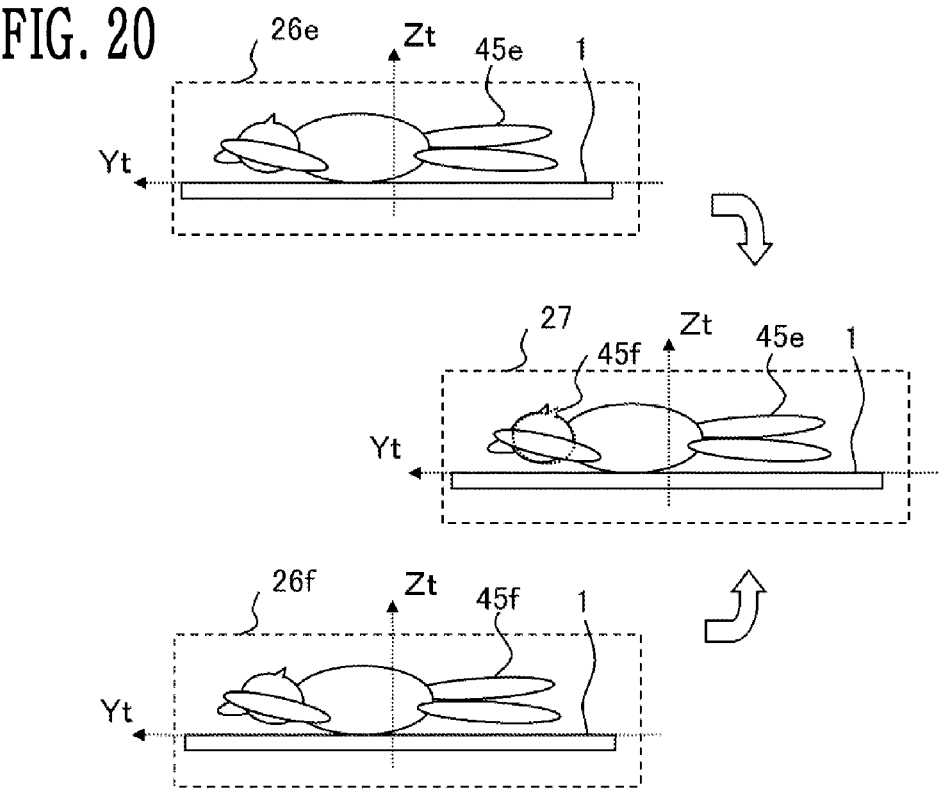
FIG. 20 is a diagram showing a three-dimensional capture image according to Embodiment 2 of the invention.

FIG. 20 is a diagram showing a three-dimensional capture image according to Embodiment 2 of the invention. The three-dimensional capture image 26*e* displayed on the display unit 72 is the reference image. Meanwhile, the three-dimensional capture image 26*f* displayed on the display unit 72 is the observed image. The patient 45*e* in the three-dimensional capture image 26*e* corresponds to the patient 45*a* in FIG. 11 and the patient 45*c* in FIG. 14. The patient 45*f* in the three-dimensional capture image 26*f* corresponds to the patient 45*b* in FIG. 12 and the patient 45*d* in FIG. 15. The comparison unit 74 compares the three-dimensional-image data corresponding to the reference image and the three-dimensional-image data corresponding to the observed image with each other according to the top-board coordinate system, and displays the comparison result on the display unit 72, for example, as the three-dimensional comparative capture image 27 in FIG. 20. The three-dimensional comparative capture image 27 is resulted from displaying a portion of the three-dimensional capture image 26*f* as the observed image (a head region of the patient 45*f* indicated by a broken line), that is mismatched from the three-dimensional capture image 26*e* as the reference image, to be overlapped with the three-dimensional capture image 26*e*.

In the above described case, when there are a plurality of imaging regions, the positional references 29 captured by the 3D cameras 4 are recognized, so that absolute positions according to the top-board coordinate system with reference to the top board 1 are determined from the captured information (three-dimensional-image data) from the individual imaging regions. As an alternative case, the positions for performing image-capturing may be calibrated so that absolute positions in the top board 1 according to the top-board coordinate system can be determined, by having previously captured the top board 1 to thereby recognize the positional references 29 of the top board 1.

In the case where a plurality of imaging regions are to be captured by a single 3D camera 4, the 3D camera 4 performs image-capturing at close timings separated for the plurality of imaging regions. The three-dimensional-image data of two imaging regions captured within a time period of several seconds are those captured at close timings. For a treatment site with which the patient 45 can be fastened firmly, even in the case of capturing a plurality of imaging regions by the single 3D camera 4, it is possible to confirm a displacement in the body position of the patient that affects the therapy.

According to the three-dimensional image capture system 30 of Embodiment 2, when a plurality of imaging regions are captured, the captured information from the plurality of imaging regions are combined, and thus, even when the imaging object can not be covered by a single imaging region, it is possible to capture the imaging object with necessary imaging regions. Also, when a blind spot occurs for the single 3D camera 4 depending on its placeable position, because of the plurality of 3D cameras 4, the blind spot for one of the 3D cameras 4 can be captured by another 3D camera 4 thereof, so that the imaging region can be enlarged. Also, in the case of a Zf-axis rotation (isocentric rotation) of the patient support table 3, for example, in a non-coplanar irradiation, or in the case of associating a large movement of the top board 1, such as, the CT-based positioning or the prior-room positioning, even when there is a plurality of imaging regions, a displacement in the body position of the patient 45 can be confirmed.

Figure 21:
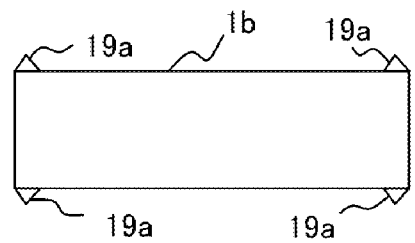
FIG. 21 is a diagram showing a second top board according to Embodiment 2 of the invention.
Figure 22:
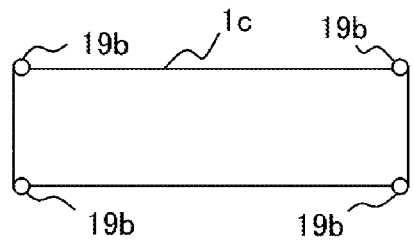
FIG. 22 is a diagram showing a third top board according to Embodiment 2 of the invention.
Figure 23:
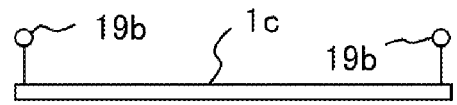
FIG. 23 is a side view of the third top board of FIG. 22.
Figure 24:
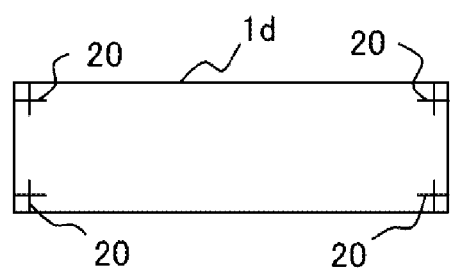
FIG. 24 is a diagram showing a fourth top board according to Embodiment 2 of the invention.
Figure 25:
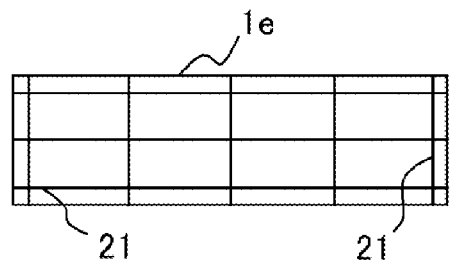
FIG. 25 is a diagram showing a fifth top board according to Embodiment 2 of the invention.

The positional references 29 of the top board 1 may be other than the corners of the top board 1 shown in FIG. 19. The positional references 29 of the top board 1 may be positional-reference members, positional-reference marks or the like provided on the top board 1. FIG. 21 is a diagram showing a second top board according to Embodiment 2 of the invention. On the top board 1b, as being extended from the circumferential portion thereof, four positional-reference members 19a are provided. FIG. 22 is a diagram showing a third top board according to Embodiment 2 of the invention and FIG. 23 is a side view of the third top board of FIG. 22. On the top board 1c, as being extended from the upper face portion thereof, four positional-reference members 19b are provided. FIG. 24 is a diagram showing a fourth top board according to Embodiment 2 of the invention. On the top board 1d, four positional-reference marks 20 are provided at portions near the corners. FIG. 25 is a diagram showing a fifth top board according to Embodiment 2 of the invention. On the top board 1e, a plurality of positional-reference lines 21 are provided on the upper face portion. The positional-reference lines 21 of the top board 1e includes a positional-reference line that is drawn in longitudinal direction and a positional-reference line 21 that is drawn in transverse direction. The positional-reference line 21 drawn in longitudinal direction is crossing to the positional-reference line 21 drawn in transverse direction.

By providing the positional-reference members 19a or 19b, the positional-reference marks 20 or the positional-reference lines 21 shown in FIG. 21 to FIG. 25, it is possible to use them as the positional references 29 other than the corners of the top board 1, so that the position information can be generated more precisely in the position-information extraction unit 73.

Embodiment 3

Figure 26:
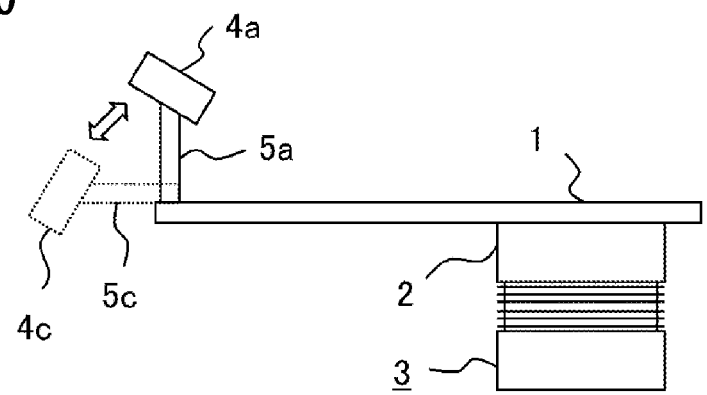
FIG. 26 is a diagram showing a 3D camera according to Embodiment 3 of the invention.

FIG. 26 is a diagram showing a 3D camera according to Embodiment 3 of the invention. The 3D camera 4 according to Embodiment 3 is configured to be movable, so that it can be changed between a position at the time of image-capturing and a position at the time of retracting. The 3D camera 4a and the supporting column 5a indicated by actual lines in FIG. 26 are in the case where they are in the positions at the time of image-capturing, and the 3D camera 4c and the supporting column 5c indicated by broken lines in FIG. 26 are in the case where they are in the positions at the time of retracting. The position of the 3D camera 4 may be changed manually or by turning the supporting column 5 using a rotary actuation device, etc.

During a radiation therapy, there is a leakage of radiation toward other than the diseased site. During a particle beam therapy, a secondary radiation is produced because of the particle beam passing a window of the irradiation port 11 or the like, or passing inside the body of the patient. Because the secondary radiation and the leakage of radiation damage the 3D camera 4, it is desirable to prevent as much as possible the 3D camera 4 from being exposed to the secondary radiation and the leakage of radiation.

In the three-dimensional image capture system 30 of Embodiment 3, since the 3D camera 4 is movably placed on the top board 1, the 3D camera 4 can be moved away from a radiation source of the secondary radiation, etc. at the time other than during image capturing. According to the three-dimensional image capture system 30 of Embodiment 3, it is possible to reduce or suppress radiation damages of low radiation-resistant electronic components provided in the 3D camera 4 because it can be moved away from the radiation source of the secondary radiation, etc., to thereby extend the life spans of the electronic components.

Figure 27:
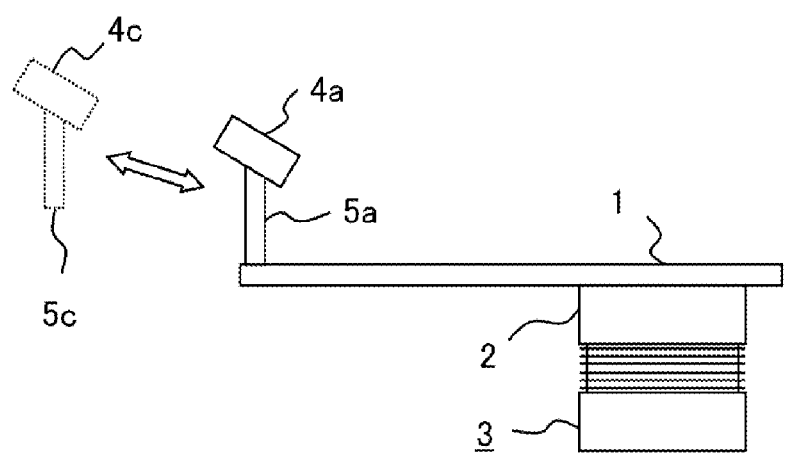
FIG. 27 is a diagram showing another 3D camera according to Embodiment 3 of the invention.

FIG. 27 is a diagram showing another 3D camera according to Embodiment 3 of the invention. The 3D camera 4 shown in FIG. 27 is placed on the top board 1 in an attachable/detachable manner. The 3D camera 4a and the supporting column 5a indicated by actual lines in FIG. 27 are in the case where they are in the positions at the time of image-capturing, and the 3D camera 4c and the supporting column 5c indicated by broken lines in FIG. 27 are in the case where they are in the intermediate positions during retracting. The retraction place for the 3D camera 4 may be selected from a corner in the treatment room that is away from the radiation source of the secondary radiation, etc., an inside of a radiation shielding box, an outside of the treatment room, and the like. Even in the case of FIG. 27, the 3D camera 4 can be moved away from the radiation source of the secondary radiation, etc. at the time other than during image capturing, and thus a similar effect to that in the case of FIG. 26 is achieved.

Embodiment 4

Figure 28:
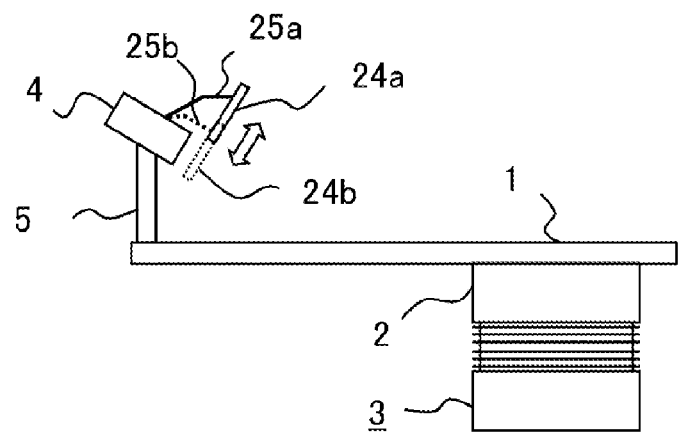
FIG. 28 is a diagram showing a 3D camera according to Embodiment 4 of the invention.

FIG. 28 is a diagram showing a 3D camera according to Embodiment 4 of the invention. The 3D camera 4 according to Embodiment 4 is configured with a shielding member 24 that is movable toward a direction from the radiation source of the secondary radiation, etc. In FIG. 28, a case is shown where a supporting member 25 connected to the shielding member 24 is attached to the 3D camera 4. A shielding member 24a and a supporting member 25a indicated by actual lines in FIG. 28 are in the case where they are in the positions at the time of image-capturing, and a shielding member 24b and a supporting member 25b indicated by broken lines in FIG. 28 are in the case where they are in the positions at the time of radiation-shielding. The position of the shielding member 24 may be changed manually or by moving the supporting member 25 using an actuation device, etc.

According to the three-dimensional image capture system 30 of Embodiment 4, since the shielding member 24 is provided that is movable toward a direction from the radiation source of the secondary radiation, etc. with respect to the 3D camera 4, it is possible to block the secondary radiation and the leakage of radiation toward the 3D camera 4 at the time other than during image capturing. Because the three-dimensional image capture system 30 of Embodiment 4 can block the secondary radiation and the leakage of radiation toward the 3D camera 4, it is possible to reduce or suppress radiation damages of low radiation-resistant electronic components provided in the 3D camera 4, to thereby extend the life spans of the electronic components.

Embodiment 5

Figure 29:
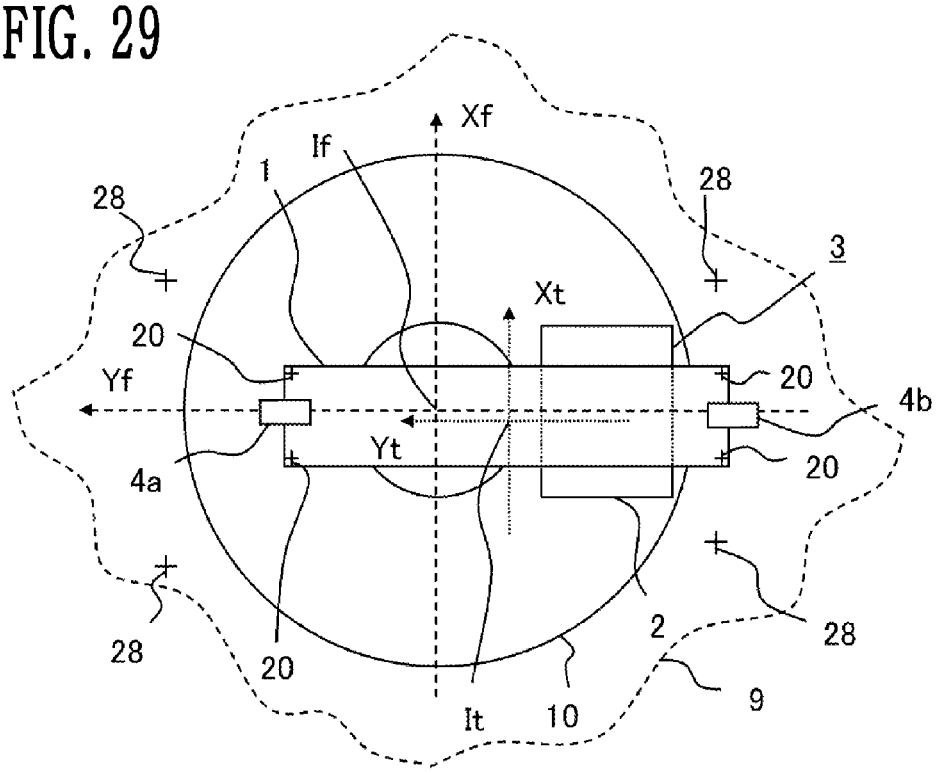
FIG. 29 is a diagram showing a main part of a three-dimensional image capture system according to Embodiment 5 of the invention.

FIG. 29 is a diagram showing a main part of a three-dimensional image capture system according to Embodiment 5 of the invention. Relative to the three-dimensional image capture system 30 of Embodiment 1 or Embodiment 2, the three-dimensional image capture system 30 of Embodiment 5 is different in that the position information based on a treatment-room coordinate system (reference coordinate system) of the patient 45 given as the imaging object, is generated from the three-dimensional-image data outputted from the 3D camera 4. As shown in FIG. 29, on the floor 9 of the treatment room, there are provided positional-reference marks 28 given as room-positional references. The positional-reference marks 28 are positional-reference members given as structure objects, printed marks or the like. Note that, in FIG. 29, there is shown a case where the positional-reference marks 28 are provided on the floor 9 of the treatment room; however, the positional-reference marks 28 are not limited to be on the floor 9 of the treatment room, and may be provided at the positions in the imaging regions of the 3D cameras 4a, 4b and on an immobile portion of a room-structure object of the treatment room, such as a ceiling, the floor 9, a wall or the like so that the positional-reference marks 28 can be captured at that positions.

An operation of the three-dimensional image capture system 30 of Embodiment 5 will be described. The three-dimensional-image processing device 6 acquires at the input unit 71, the three-dimensional-image data outputted from the 3D cameras 4a, 4b. In the three-dimensional-image data acquired at the input unit 71, the positional-reference marks 28 and also the positional-reference marks 20 are being captured. The three-dimensional-image processing device 6 takes, at the position-information extraction unit 73, a correlation between the treatment-room coordinate system with reference to the treatment room and the three-dimensional position information of the patient 45, for each of the three-dimensional-image data of the respective 3D cameras 4a, 4b, to thereby generate the position information based on the treatment-room coordinate system of the patient 45 given as the imaging object. The position information based on the treatment-room coordinate system of the patient 45 is treatment-room-coordinate-system position information (reference-coordinate-system position information). The position-information extraction unit 73 generates the position information of the patient 45 using as starting points, the coordinates of the positional-reference marks 28 shown in FIG. 29. The three-dimensional-image processing device 6 generates at the information combining unit 76, combined three-dimensional-image data in which the three-dimensional-image data of the 3D camera 4a and the three-dimensional-image data of the 3D camera 4b are combined, to thereby output the three-dimensional capture image to the display unit 72.

The three-dimensional capture image displayed on the display unit 72 is based on the combined three-dimensional-image data that is associated with the treatment-room coordinate system. Thus, the three-dimensional capture image displayed on the display unit 72 is associated with the treatment-room coordinate system and is given as a three-dimensional capture image in which the three-dimensional-image data is consolidated with the treatment-room-coordinate-system-position information. Further, the three-dimensional-image processing device 6 stores in the storage unit 75, a plurality of three-dimensional-image data inputted from the input unit 71 and the combined three-dimensional-image data. The three-dimensional-image processing device 6 compares with each other, at the comparison unit 74, two specified three-dimensional-image data, that is, two three-dimensional-image data having been image-captured at different timings, and displays the comparison result on the display unit 72. Instead, the comparison unit 74 may compare with each other, two combined three-dimensional-image data having been captured at different timings.

Figure 30:
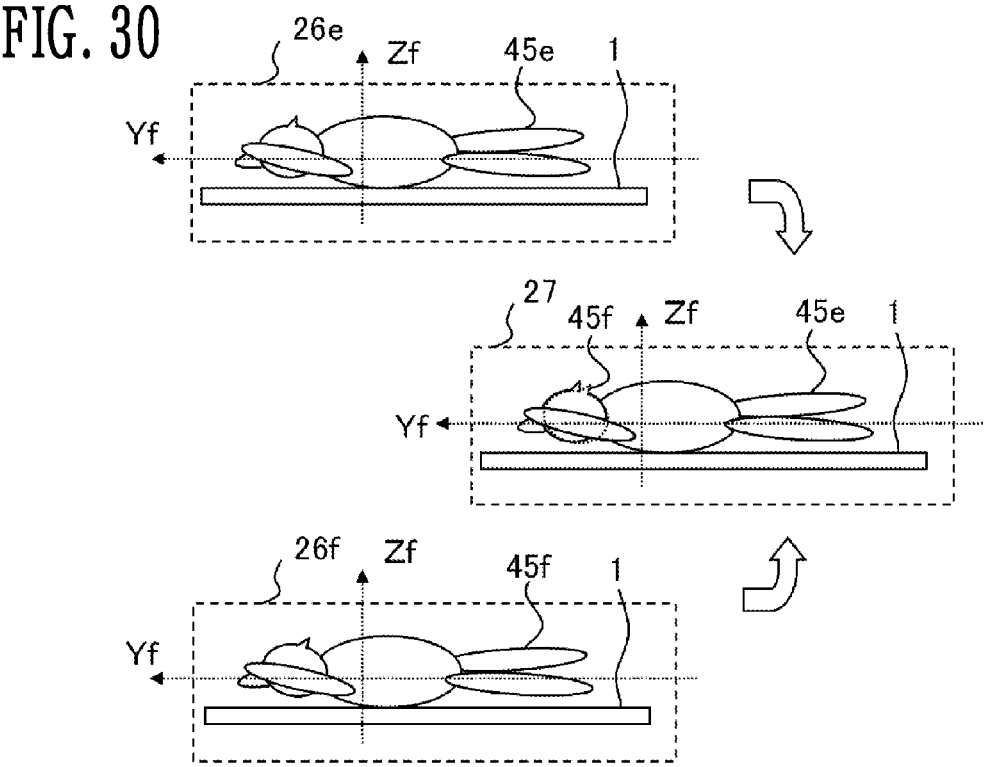
FIG. 30 is a diagram showing a three-dimensional capture image according to Embodiment 5 of the invention.

FIG. 30 is a diagram showing a three-dimensional capture image according to Embodiment 5 of the invention. The three-dimensional capture image 26e displayed on the display unit 72 is the reference image. Meanwhile, the three-dimensional capture image 26f displayed on the display unit 72 is the observed image. The patient 45e in the three-dimensional capture image 26e corresponds to the patient 45a in FIG. 11 and the patient 45c in FIG. 14. The patient 45f in the three-dimensional capture image 26f corresponds to the patient 45b in FIG. 12 and the patient 45d in FIG. 15. The comparison unit 74 compares the three-dimensional-image data corresponding to the reference image and the three-dimensional-image data corresponding to the observed image with each other according to the treatment-room coordinate system, and displays the comparison result on the display unit 72, for example, as the three-dimensional comparative capture image 27 in FIG. 30. The three dimensional comparative capture image 27 is resulted from displaying a portion of the three-dimensional capture image 26f as the observed image (a head region of the patient 45f indicated by a broken line), that is mismatched from the three-dimensional capture image 26e as the reference image, to be overlapped with the three-dimensional capture image 26e.

In the above described case, when there are a plurality of imaging regions, the positional references 29 captured by the 3D cameras 4 are recognized, so that absolute positions according to the treatment-room coordinate system with reference to the treatment room are determined from the captured information from the individual imaging regions (three-dimensional-image data). As an alternative case, the positions for performing image-capturing may be calibrated so that absolute positions according to the treatment-room coordinate system can be determined, by having previously captured the top board 1 so that the positional-reference marks 28 of the treatment room were caught simultaneously, to thereby recognize the positional-reference marks 28 of the treatment room and the positional-reference marks 20 of the top board 1.

The three-dimensional image capture system 30 of Embodiment 5 can confirm a displacement in the body position of the patient 45 in the treatment-room coordinate system after completion of the image-matching positioning, without using an X-ray radiographic device. Because the three-dimensional image capture system 30 of Embodiment 5 can confirm a displacement in the body position of the patient 45 in the treatment-room coordinate system, the correlations with the configuration devices of the radiation irradiation apparatus (particle beam irradiation apparatus 58, etc.) become clear, and thus the positioning condition of the patient can be recognized more precisely. According to the radiation therapy system (particle beam therapy system 51, etc.) provided with the three-dimensional image capture system 30 of Embodiment 5, the correlations of the displacement in the body position of the patient 45 with the configuration devices of the radiation irradiation apparatus (particle beam irradiation apparatus 58, etc.) become more clear than those of the system using the three-dimensional image capture system 30 of Embodiment 1 or Embodiment 2. Thus, the radiation can be radiated with a dose distribution planned in the treatment plan, more accurately.

Figure 31:
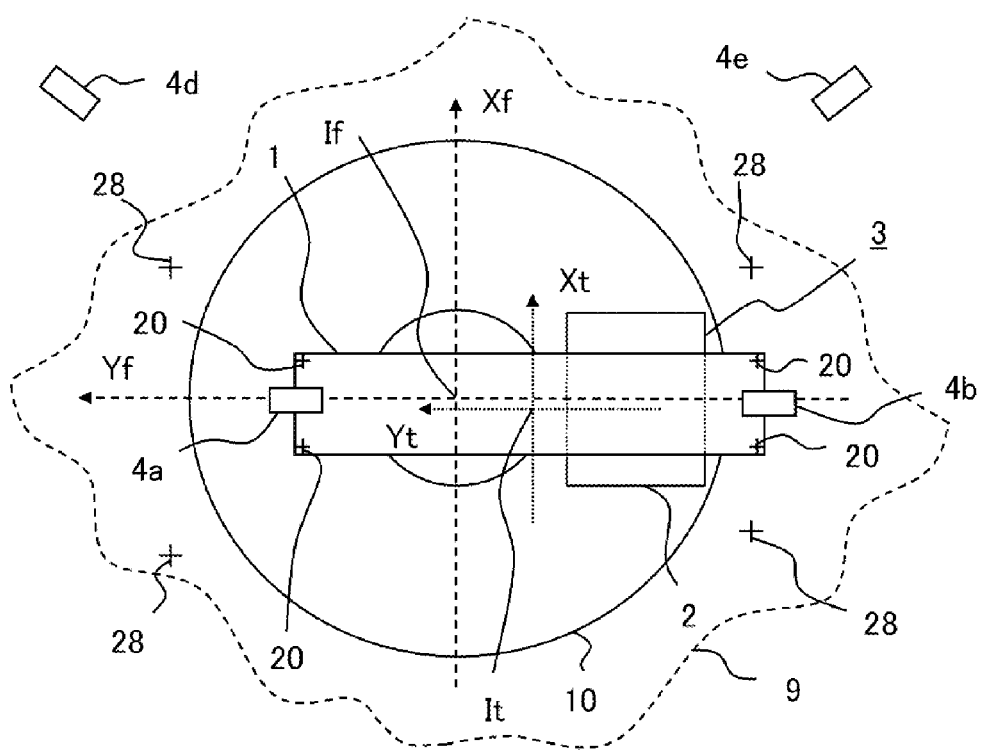
FIG. 31 is a diagram showing a main part of another three-dimensional image capture system according to Embodiment 5 of the invention.

Note that in the case where the positional-reference marks 28 of the treatment room and the positional-reference marks 20 of the top board 1 can not be captured simultaneously due to interruption of the patient 45, other 3D cameras 4d, 4e may be provided in the treatment room as shown in FIG. 31. The position-information extraction unit 73 calculates from the three-dimensional-image data for positional reference outputted from the other 3D cameras 4d, 4e, coordinates of the positional-reference marks 20 (positional references of the top board 1) in the treatment-room coordinate system (reference coordinate system) to thereby generate treatment-room coordinate-system position information (reference-coordinate-system position information). By placing the 3D cameras 4d, 4e away from the top board 1, the positional-reference marks 28 of the treatment room and the positional-reference marks 20 of the top board 1 can be captured simultaneously, so that a displacement in the body position of the patient 45 in the treatment-room coordinate system can be surely confirmed. Note that, in FIG. 31, there is shown a case where the positional-reference marks 28 are provided on the floor 9 of the treatment room; however, the positional-reference marks 28 are not limited to be on the floor 9 of the treatment room, and may be provided at the positions in the imaging regions of the other 3D cameras 4d, 4e and on an immobile portion of a room-structure object of the treatment room, such as a ceiling, the floor 9, a wall or the like so that the positional-reference marks 28 can be captured at that positions. That is, the positional-reference marks 28 in FIG. 31 may be not placed in the positions within the imaging regions of the 3D cameras 4a, 4b placed on the top board 1, so that positional flexibility in placing the positional-reference marks 28 can be enhanced.

Note that the description has been made in the case where the positional-reference marks 20 are provided on the top board 1; however, the corners illustrated in FIG. 19 may be used as the positional references 29, or the top board provided with the positional-reference members 19a or 19b, or the positional-reference lines 21, shown in FIG. 21, FIG. 22 or FIG. 25, may instead be used as well. Meanwhile, in the case of the prior-room positioning, positional-reference marks 28 are provided in a room in which the image-matching positioning is to be performed, and then, using their correlations with the positional-reference marks 28 of the treatment room, the actuation device 2 is controlled on the basis of the position/posture information at the time of the image-matching positioning, so that the position/posture at the time of the image-matching positioning can be reproduced.

It should be noted that unlimited combination of the respective embodiments, any modification of the embodiments and any omission in the embodiments may be made appropriately in the present invention without departing from the scope of the invention.

DESCRIPTION OF REFERENCE NUMERALS AND SIGNS 1, 1a, 1b, 1c, 1d, 1e: top boards, 3: patient support table, 4, 4a, 4b, 4c, 4d, 4e: 3D cameras, 6: three-dimensional-image processing device, 9: floor, 19a, 19b: positional-reference members, 20: positional-reference mark, 21: positional-reference line, 22a, 22b: imaging regions, 24, 24a, 24b: shielding members, 26, 26a, 26b, 26c, 26d, 26e, 26f: three-dimensional capture images (three-dimensional images), 27: three-dimensional comparative capture image (comparison result), 28: positional-reference mark (room-positional reference), 29: positional reference, 30: three-dimensional image capture system, 31: charged particle beam, 45: patient, 52: beam generation apparatus, 54: charged particle accelerator, 58, 58a, 58b: particle beam irradiation apparatuses, 59: beam transport system, 72: display unit, 73: position-information extraction unit, 74: comparison unit, 76: information combining unit.

The invention claimed is:

1. A three-dimensional image capture system for image-capturing a patient laid on a top board of a patient support table, comprising:

a three-dimensional measuring device that is placed on the top board of the patient support table, and performs image-capturing of the patient (i) after completion of image-matching positioning, (ii) without using an X-ray, and (iii) after movement of the patient, on the patient support table, to a therapeutic irradiation position, to thereby generate three-dimensional-image data; and a processing device, including a display device, configured to:
generate, from the three-dimensional-image data, a three-dimensional image associated with a reference coordinate system which is a top-board coordinate system with reference to the top board or a room coordinate system with reference to a floor of a room in which the patient support table is placed, and that displays the three-dimensional image;

take a correlation between the reference coordinate system and three-dimensional position information of the patient in the three-dimensional-image data, to thereby generate reference-coordinate-system position information of the patient based on the reference coordinate system; and display, on the display device of the processing device, the three-dimensional image in which the three-dimensional-image data and the reference-coordinate-system position information are consolidated; and display, on the display device, a reference image that is a three-dimensional image captured in a condition where a diseased-site region of the patient is being positioned relative to the top board, and an observed image that is a three-dimensional image captured at a timing different to a timing at which the reference image was captured.

2. The three-dimensional image capture system of claim 1, wherein
the processing device is further configured to combine a plurality of image data, each being the three-dimensional-image data, captured individually for a plurality of imaging regions by the three-dimensional measuring device at close timings, on the basis of the reference-coordinate-system position information generated by the processing device, to thereby generate combined three-dimensional-image data, and
wherein the display device, of the processing device, regards as the three-dimensional image, a combined three-dimensional image in which the combined three-dimensional-image data and the reference-coordinate-system position information are consolidated.

3. The three-dimensional image capture system of claim 2, wherein the processing device displays, on the display device, the reference image and the observed image captured at the different timings, to be overlapped with each other in such a manner that their same coordinate in the reference coordinate system is placed at a same position.

4. The three-dimensional image capture system of claim 2, wherein the processing device is further configured to compare, according to the reference coordinate system, first three-dimensional-image data given as the three-dimensional image-data or the combined three-dimensional-image data captured at a first timing, with second three-dimensional-image data given as the three-dimensional image-data or the combined three-dimensional-image data captured at a timing later than the first timing, and that displays a comparison result on the display device.

5. The three-dimensional image capture system of claim 1, comprising a plurality of three-dimensional measuring devices as the three-dimensional measuring device,
- wherein the processing device is configured to combine a plurality of image data, each being the three-dimensional-image data, captured individually for a plurality of imaging regions by the plurality of three-dimensional measuring devices at substantially the same timings, on the basis of the reference-coordinate-system position information generated by the position-information extraction unit, to thereby generate combined three-dimensional-image data, and
- wherein the display device, of the processing device, regards as the three-dimensional image, combined three-dimensional image in which the combined three-dimensional-image data and the reference-coordinate-system position information are consolidated.

6. The three-dimensional image capture system of claim 5, wherein the processing device displays, on the display device, the reference image and the observed image captured at the different timings, to be overlapped with each other in such a manner that their same coordinate in the reference coordinate system is placed at a same position.

7. The three-dimensional image capture system of claim 5, wherein the processing device is further configured to compare, according to the reference coordinate system, first three-dimensional-image data given as the three-dimensional image-data or the combined three-dimensional-image data captured at a first timing, with second three-dimensional-image data given as the three-dimensional image-data or the combined three-dimensional-image data captured at a timing later than the first timing, and that displays a comparison result on the display device.

8. The three-dimensional image capture system of claim 1, wherein the processing device displays, on the display device, the reference image and the observed image captured at the different timings, to be overlapped with each other in such a manner that their same coordinate in the reference coordinate system is placed at a same position.

9. The three-dimensional image capture system of claim 1, wherein the processing device is configured to compare, according to the reference coordinate system, first three-dimensional-image data given as the three-dimensional image-data or the combined three-dimensional-image data captured at a first timing, with second three-dimensional-image data given as the three-dimensional image-data or the combined three-dimensional-image data captured at a timing later than the first timing, and that displays a comparison result on the display device.

10. The three-dimensional image capture system of claim 9, wherein the processing device displays a differential image that is a difference according to the reference coordinate system between the first three-dimensional-image data and the second three-dimensional-image data, to be overlapped with the reference image based on the first three-dimensional-image data or the observed image based on the second three-dimensional-image data.

11. The three-dimensional image capture system of claim 1, wherein the reference coordinate system is the top-board coordinate system and the processing device generates the reference-coordinate-system position information on the basis of coordinates of a plurality of positional references on the top board.

12. The three-dimensional image capture system of claim 1, wherein the reference coordinate system is the room coordinate system, and the processing device generates the reference-coordinate-system position information on the basis of: coordinates of a plurality of room-positional references provided in an imaging region of the three-dimensional measuring device on an immobile portion of a room-structure object of the room in which the patient support table is placed; and coordinates of a plurality of positional references on the top board.

13. The three-dimensional image capture system of claim 12, further comprising another three-dimensional measuring device that image-captures simultaneously, at least one of the plurality of room-positional references provided on the immobile portion of the room-structure object and at least one of the plurality of positional references of the top board, to thereby generate three-dimensional-image data for positional reference,
- wherein the processing device calculates from the three-dimensional-image data for positional reference, coordinates at the positional references in the reference coordinate system, to thereby generate the reference-coordinate-system position information.

14. The three-dimensional image capture system of claim 1, wherein the positional references are positional-reference members provided on the top board.

15. The three-dimensional image capture system of claim 1, wherein the positional references are positional-reference marks provided on the top board.

16. The three-dimensional image capture system of claim 1, wherein the positional references are positional-reference lines provided on the top board.

17. The three-dimensional image capture system of claim 1, wherein the three-dimensional measuring device is movably placed on the top board.

18. The three-dimensional image capture system of claim 1, wherein the three-dimensional measuring device is placed on the top board in an attachable/detachable manner.

19. The three-dimensional image capture system of claim 1, wherein the three-dimensional measuring device has a movably-placed shielding member.

20. A particle beam therapy system comprising: a beam generation apparatus that generates a charged particle beam and accelerates it up to a given energy using an accelerator; a beam transport system that transports the charged particle beam accelerated by the beam generation apparatus; a particle beam irradiation apparatus that radiates the charged particle beam transported by the beam transport system to a patient; and a three-dimensional image capture system that image-captures the patient to which the charged particle beam is to be radiated;
- wherein the three-dimensional image capture system is the three-dimensional image capture system of claim 1.

* * * * *